United States Patent
Wagner et al.

(10) Patent No.: US 9,572,311 B2
(45) Date of Patent: Feb. 21, 2017

(54) SOYBEAN TRANSGENIC EVENT MON87705 AND METHODS FOR DETECTION THEREOF

(71) Applicant: Monsanto Technology LLC, St. Louis, MO (US)

(72) Inventors: Nicholas Wagner, Sacramento, CA (US); Wen C. Burns, Chesterfield, MO (US); Eric J. Godsy, Millstadt, IL (US); Peter D. Roberts, Benicia, CA (US)

(73) Assignee: Monsanto Technology LLC, St. Louis, MO (US)

( * ) Notice: Subject to any disclaimer, the term of this patent is extended or adjusted under 35 U.S.C. 154(b) by 533 days.

(21) Appl. No.: 13/930,925

(22) Filed: Jun. 28, 2013

(65) Prior Publication Data

US 2013/0309672 A1 Nov. 21, 2013

Related U.S. Application Data

(62) Division of application No. 13/670,136, filed on Nov. 6, 2012, now Pat. No. 8,692,080, which is a division of application No. 12/568,321, filed on Sep. 28, 2009, now Pat. No. 8,329,989.

(60) Provisional application No. 61/100,859, filed on Sep. 29, 2008.

(51) Int. Cl.
| | |
|---|---|
| *C12N 15/82* | (2006.01) |
| *A01H 5/00* | (2006.01) |
| *A23D 9/00* | (2006.01) |
| *C12Q 1/68* | (2006.01) |
| *C07H 21/04* | (2006.01) |
| *C12N 15/11* | (2006.01) |

(52) U.S. Cl.
CPC ........ *A01H 5/00* (2013.01); *A23D 9/00* (2013.01); *A23K 50/80* (2016.05); *A23L 11/00* (2016.08); *C07H 21/04* (2013.01); *C12N 15/11* (2013.01); *C12N 15/8247* (2013.01); *C12Q 1/6895* (2013.01)

(58) Field of Classification Search
None
See application file for complete search history.

(56) References Cited

U.S. PATENT DOCUMENTS

| | | | |
|---|---|---|---|
| 4,557,734 A | 12/1985 | Schwab et al. | |
| 5,454,842 A | 10/1995 | Poirier et al. | |
| 5,475,099 A | 12/1995 | Knauf et al. | |
| 5,500,361 A | 3/1996 | Kinney | |
| 5,602,320 A | 2/1997 | Rhodes | |
| 5,627,061 A | 5/1997 | Barry et al. | |
| 5,633,435 A | 5/1997 | Barry et al. | |
| 5,714,670 A | 2/1998 | Fehr et al. | |
| 5,723,595 A | 3/1998 | Thompson et al. | |
| 5,723,761 A | 3/1998 | Voelker et al. | |
| 5,850,026 A | 12/1998 | Debonte et al. | |
| 5,888,947 A | 3/1999 | Lambert et al. | |
| 5,891,203 A | 4/1999 | Ball et al. | |
| 5,955,329 A | 9/1999 | Yuan et al. | |
| 5,955,650 A | 9/1999 | Hitz | |
| 6,013,114 A | 1/2000 | Hille et al. | |
| 6,150,512 A | 11/2000 | Yuan | |
| 6,331,664 B1 | 12/2001 | Rubin-Wilson et al. | |
| 6,369,296 B1 | 4/2002 | Ratcliff et al. | |
| 6,372,965 B1 | 4/2002 | Lightner et al. | |
| 6,380,462 B1 | 4/2002 | Kridl | |
| 6,384,301 B1 | 5/2002 | Martinell et al. | |
| 6,506,559 B1 | 1/2003 | Driver et al. | |
| 6,573,099 B2 | 6/2003 | Graham | |
| 7,166,771 B2 | 1/2007 | Eenennaam et al. | |
| 7,566,813 B2 | 7/2009 | Voelker et al. | |
| 7,601,888 B2 | 10/2009 | Fillatti et al. | |
| 2002/0034814 A1 | 3/2002 | Atabekov et al. | |
| 2003/0049835 A1 | 3/2003 | Helliwell et al. | |
| 2003/0135882 A1 | 7/2003 | Metzlaff et al. | |
| 2003/0172399 A1 | 9/2003 | Fillatti | |
| 2004/0006792 A1 | 1/2004 | Fillatti et al. | |
| 2004/0107459 A1 | 6/2004 | Lardizabal et al. | |
| 2004/0107460 A1 | 6/2004 | Fillatti et al. | |
| 2004/0126845 A1 | 7/2004 | Eenennaam et al. | |
| 2005/0034190 A9 | 2/2005 | Fillatti et al. | |
| 2006/0080750 A1 | 4/2006 | Fillatti et al. | |

(Continued)

FOREIGN PATENT DOCUMENTS

| | | | |
|---|---|---|---|
| AU | 200321427 A1 | 10/2003 | |
| AU | 2004276819 B2 | 4/2005 | |

(Continued)

OTHER PUBLICATIONS

Ayele et al, Genome Research 15(4): 487-495, 2005.*
Anklam et al., "Analytical methods for detection and determination of genetically modified organisms in agricultural crops and plant-derived food products," *Eur Food Res Technol*, 214:3-26 (2002).
Ayele et al., "Whole genome shotgun sequencing of *Brassica oleracea* and its application to gene discovery and annotation in *Arabidopsis*," *Genome Research*, 15(4):487-495 (2005).
Bosher et al., "RNA Interference Can Target Pre-mRNA: Consequences for Gene Expression in a *Caenorhabditis elegans* Operon," *Genetics*, 153:1245-1256 (1999).

(Continued)

Primary Examiner — Elizabeth McElwain
(74) Attorney, Agent, or Firm — Arnold & Porter Kaye Scholer LP; Chunping Li; David Marsh

(57) ABSTRACT

The present invention provides a transgenic soybean event MON87705, and cells, seeds, and plants comprising DNA diagnostic for the soybean event. The invention also provides compositions comprising nucleotide sequences that are diagnostic for said soybean event in a sample, methods for detecting the presence of said soybean event nucleotide sequences in a sample, probes and primers for use in detecting nucleotide sequences that are diagnostic for the presence of said soybean event in a sample, growing the seeds of such soybean event into soybean plants, and breeding to produce soybean plants comprising DNA diagnostic for the soybean event.

14 Claims, 2 Drawing Sheets

(56) References Cited

U.S. PATENT DOCUMENTS

| | | |
|---|---|---|
| 2006/0206963 A1 | 9/2006 | Voelker et al. |
| 2007/0074305 A1 | 3/2007 | Eenennaam et al. |
| 2007/0214516 A1 | 9/2007 | Fillatti et al. |
| 2008/0222756 A1 | 9/2008 | Fillatti et al. |
| 2009/0119805 A1 | 5/2009 | Fillatti et al. |
| 2009/0151029 A1 | 6/2009 | Voelker et al. |

FOREIGN PATENT DOCUMENTS

| | | |
|---|---|---|
| AU | 2007215181 A2 | 8/2007 |
| BR | PI 0414743-0 A | 11/2006 |
| CA | 2 479 587 A1 | 10/2003 |
| CA | 2 540 049 A1 | 4/2005 |
| CA | 2 641 264 A1 | 8/2007 |
| CN | 1655669 A | 8/2005 |
| CN | 1886042 A | 12/2006 |
| CN | 101421406 A | 4/2009 |
| EP | 0 959 133 A1 | 11/1999 |
| EP | 1 484 959 A | 12/2004 |
| EP | 1 670 307 A | 6/2006 |
| EP | 1 984 508 A | 10/2008 |
| IN | 2255/DELNP/2006 | 7/2007 |
| IN | 1430/CHENP/2008 | 11/2008 |
| IN | 228211 | 1/2009 |
| KR | 1020060063997 A | 6/2006 |
| KR | 1020080009243 A | 1/2008 |
| MX | PA04009134 A | 1/2005 |
| WO | WO 93/11245 A1 | 6/1993 |
| WO | WO 94/10189 A1 | 5/1994 |
| WO | WO 94/11516 A1 | 5/1994 |
| WO | WO 96/06936 A1 | 3/1996 |
| WO | WO 98/05770 A2 | 2/1998 |
| WO | WO 98/30083 A1 | 7/1998 |
| WO | WO 98/46776 A2 | 10/1998 |
| WO | WO 98/53083 A1 | 11/1998 |
| WO | WO 98/56239 A1 | 12/1998 |
| WO | WO 99/15682 A2 | 4/1999 |
| WO | WO 99/32619 A1 | 7/1999 |
| WO | WO 99/49029 A1 | 9/1999 |
| WO | WO 99/53050 A1 | 10/1999 |
| WO | WO 99/61631 A1 | 12/1999 |
| WO | WO 99/64579 A2 | 12/1999 |
| WO | WO 00/07432 A1 | 2/2000 |
| WO | WO 00/18880 A2 | 4/2000 |
| WO | WO 00/44895 A1 | 8/2000 |
| WO | WO 00/44914 A1 | 8/2000 |
| WO | WO 00/68374 A1 | 11/2000 |
| WO | WO 01/11061 A2 | 2/2001 |
| WO | WO 01/14538 A2 | 3/2001 |
| WO | WO 01/34822 A2 | 5/2001 |
| WO | WO 01/35726 A1 | 5/2001 |
| WO | WO 01/36598 A1 | 5/2001 |
| WO | WO 01/70949 A1 | 9/2001 |
| WO | WO 01/79499 A1 | 10/2001 |
| WO | WO 02/04581 A1 | 1/2002 |
| WO | WO 02/15675 A1 | 2/2002 |
| WO | WO 02/059336 A2 | 8/2002 |
| WO | WO 02/081711 A1 | 10/2002 |
| WO | WO 02/088301 A2 | 11/2002 |
| WO | WO 03/080802 A2 | 10/2003 |
| WO | WO 04/000871 A2 | 12/2003 |
| WO | WO 04/001000 A2 | 12/2003 |
| WO | WO 04/001001 A2 | 12/2003 |
| WO | WO 2005/030982 A2 | 4/2005 |
| WO | WO 2007/095243 A2 | 8/2007 |
| WO | WO 2007/106728 A2 | 9/2007 |

OTHER PUBLICATIONS

Bouchon et al., "Oil Distribution in Fried Potatoes Monitored by Infrared Microspectroscopy," *Journal of Food Science*, 66(7):918-923 (2001).

Buhr et al., "Ribozyme Termination of RNA Transcripts Down-Regulate Seed Fatty Acid Genes in Transgenic Soybean," *The Plant Journal*, 30(2):155-163 (2002).

Burch-Smith et al., "Applications and advantages of virus-induced gene silencing for gene function studies in plants," *The Plant Journal*, 39:734-746(2004).

Cartea et al., "Comparison of Sense and Antisense Methodologies for Modifying the Fatty Acid Composition of *Arabidopsis thaliana* Oilseed," *Plant Science*, 136:181-194 (1998).

Chapman et al., "Transgenic cotton plants with increased seed oleic acid content," *JAOCS*, 78:941-947 (2001).

Chuang et al., "Specific and Heritable Genetic Interference by Double-Stranded RNA in *Arabidopsis thaliana*," *PNAS*, 97(9):4985-4990 (2000).

Clark-Walker et al., "Location of Transcriptional Control Signals and Transfer RNA Sequences in *Torulopsis glabrata* Mitochondrial DNA," *EMBO (European Molecular Biology Organization) Journal*, 4(2):465-473 (1985).

Cogoni, C. et al., "Post-Transcriptional Gene Silencing Across Kingdoms," *Curr. Opin. Gen. & Devel.*, 10(6):638-643 (2000).

Colliver et al., "Differential modification of flavonoid and isoflavonoid biosynthesis with an antisense chalcone synthase construct in transgenic *Lotus corniculatus*," *Plant Mol. Biol.*, 35:509-522 (1997).

Crossway, A. et al., "Integration of Foreign DNA Following Microinjection of Tobacco Mesophyll Protoplasts," *Mol. Gen. Genet.*, 202(2):179-185 (1986).

Database Accession No. p65U (Jun. 22, 2007) (3 pages).

Database EM_GSS 'Online! EMBL Heidelberg, Germany; AL063932, May 29, 1999, Genoscope; "Drosophila melanogaster genome survey sequence TET3 end of BAC: BACR8010," abstract.

Database EM_GSS 'Online! EMBL Heidelberg, Germany; AL069706, May 29, 1999, Genoscope: "Drosophila melanogaster genome survey sequence T7 end of BAC: BACR29B23," abstract.

Database EM_GSS 'Online! EMBL Heidelberg, Germany; AL071390, May 29, 1999, Genoscope: "Drosophila melanogaster genome surface sequence TET3 end of BAC: BACR32MO5," abstract.

Database EM_GSS 'Online! EMBL Heidelberg, Germany; AL105179, Jul. 26, 1999, Genoscope: "Drosophila melanogaster genome survey sequence T7 end of BAC: BACN13A12," abstract.

Database EM_GSS 'Online! EMBL Heidelberg, Germany; AL108811, Jul. 26, 1999, Genoscope: "Drosophila melanogaster genome survey sequence SP6 end of BAC BACN37D10," abstract.

Database EM_NEW 'Online! EMBL Heidelberg, Germany; AB026636, May 7, 1999, Sato S. et al.: "Arabidopsis thaliana genomic DNA, chromosome 3, TAC clone: K14A17," abstract.

Database EMEST_PLN 'Online! EMBL Heidelberg, Germany; AW397948, Feb. 8, 2000, Shoemaker R. et al.: "Public soybean EST project," abstract.

Database EM-NEW 'Online! EMBL Heidelberg, Germany; AB022220, Jan. 15, 1999, Sato S. et al.: "Arabidopsis thaliana genomic DNA, chromosome 3, P1 clone: MLN21," abstract.

Database EMPLN 'Online! EMBL Heidelberg, Germany; AC004705, May 21, 1998, Lin X et al.: "Sequence and analysis of chromosome 2 of the plant Arabidopsis thaliana," abstract.

Database EMPLN 'Online! EMBL Heidelberg, Germany; AL161581, Mar. 15, 2000, Weichselgartner M. et al.: "Arabidopsis thaliana chromosome 4, contig fragment No. 77," abstract.

Daun, "Effect of Frost Damage on the Quality of Canola (*B. napus*)," *JAOCS*, 62(4):715-719 (1985).

DeLuca, "Molecular characterization of secondary metabolic pathways," *AgBiotech News and Information*, 5(6):225N-229N (1993).

Dörmann, P. et al., "Accumulation of Palmitate in Arabidopsis Mediated by the Acyl-Acyl Carrier Protein Thioesterase FATB1," *Plant Physiology*, 123:637-643 (2000).

Duffield, J. et al., "U.S. Biodiesel Development: New Markets for Conventional and Genetically Modified Agricultural Products," *Economic Research Service USDA*, pp. 1-31 (1998).

Dunn, R. et al., "Recent Advances in the Development of Alternative Diesel Fuel from Vegetable Oils and Animal Fats," *Recent Res. Devel. in Oil Chem.*, 1:31-56 (1997).

Erhan, S. et al., "Lubricant Basestocks from Vegetable Oils," *Industrial Crops and Products*, 11:277-282 (2000).

European Search Report issued on Mar. 16, 2012, in European Patent Application No. 09816983.2.

(56) References Cited

OTHER PUBLICATIONS

Fire, A. et al., "Potent and Specific Genetic Interference by Double-Stranded RNA in *Caenorhabditis elegans*," *Nature*, 391:806-811 (1998).
GenBank Accession No. BF324940, EST name su29c08.y1 (Jul. 13, 2004) (2 pages).
GenBank Accession No. BH684437, GSS name BOHXS88TR (Feb. 19, 2002) (2 pages).
Halpin, C. et al., "Enabling Technologies for Manipulating Multiple Genes on Complex Pathways," *Plant Molecular Biology*, 47:295-310 (2001).
Hamada, T. et al., "Modification of Fatty Acid Composition by Over- and Antisense-Expression of a Microsomal ω-3 Fatty Acid Desaturase Gene in Transgenic Tobacco," *Transgenic Research*, 5(2), 115-121 (1996).
Hamilton et al., "A Transgene with Repeated DNA Causes High Frequency, Post-Transcriptional Suppression of ACC-Oxidase Gene Expression in Tomato," *The Plant Journal*, 15(6):737-746 (1998).
International Preliminary Examination Report in PCT/US00/22613 (published as WO 01/14538), dated Dec. 6, 2001.
International Preliminary Examination Report in PCT/US03/08610 (published as WO 03/080802), dated Mar. 4, 2004.
International Preliminary Examination Report in PCT/US03/19437 (published as WO 2004/001000), dated Jul. 27, 2004.
International Preliminary Examination Report in PCT/US03/19445 (published asWO 2004/001001), dated Nov. 4, 2004.
International Preliminary Report on Patentability in PCT/US2004/31605 (published as WO 2005/030982), dated Mar. 27, 2006.
International Preliminary Report on Patentability in PCT/US2007/003823 (published as WO 2007/095243), dated Aug. 19, 2008.
International Search Report in PCT/US00/22613 (published as WO 01/14538), mailed Apr. 26, 2001.
International Search Report in PCT/US03/08610 (published as WO 03/080802), mailed Nov. 13, 2003.
International Search Report in PCT/US03/19437 (published as WO 2004/001000), dated Jun. 21, 2004.
International Search Report in PCT/US03/19445 (published asWO 2004/001001), mailed Apr. 9, 2004.
International Search Report in PCT/US2004/31605 (published as WO 2005/030982), mailed Jul. 12, 2005.
International Search Report in PCT/US2007/003823 (published as WO 2007/095243), mailed Jul. 12, 2007.
International Search Report mailed on Dec. 30, 2009, in International Application No. PCT/US2009/58591.
Jaworski et al., "Industrial oils from transgenic plants," *Current Opinion in Plant Biology*, 6(2):178-184 (2003).
Lang et al., "Preparation and characterization of bio-diesels from various bio-oils," *Bioresource Technology*, 80:53-62 (2001).
Lee et al., "Antisense Expression of the CK2 α-Subunit Gene in *Arabidopsis*. Effects on Light-Regulated Gene Expression and Plant Growth," *Plant Physiology*, 119:989-1000 (1999).
Levin et al., "Methods of Double-Stranded RNA-Mediated Gene Inactivation in *Arabidopsis* and Their Use to Define an Essential Gene in Methionine Biosynthesis," *Plant Mol. Biol.*, 44(6):759-775 (2000).
Lewin, B., "How Did Interrupted Genes Evolve?," *Genes*, 2nd Edition, pp. 333-337 (1985).
Martin et al., "A comparison of Oleic Acid Metabolism n the Soybean (Glycine max [L.] Merr.) Genotypes Williams and A5, a mutant with decreased linoleic acid in the seed," *Plant Phys.*, 61:41-44 (1986).
Martinez-Rivas et al., "Oxygen-independent temperature regulation of the microsomal oleate desaturase (FAD2) activity in developing sunflower (*Helianthus annuus* ) seeds," *Physiologia Plantarum*, 117:179-185 (2003).
Matzke, M.A. et al., "RNA-Based Silencing Strategies in Plants," *Curr. Opin. Gen. & Devel.*, 11(2):221-227 (2001).

McCormick et al, "Effect of Humidity on Heavy-Duty Transient Emissions from Diesel and Natural Gas Engines at High Altitude," *Journal of the Air & Waste Management Association*, 47:784-791 (1997).
Mensink, R. et al., "Effect of Dietary Fatty Acids on Serum Lipids and Lipoproteins: A Meta-Analysis of 27 Trials," *Arteriosclerosis and Thrombosis*, 12(8):911-919 (1992).
Montgomery, M.K. et al., "RNA as a Target of Double-Stranded RNA-Mediated Genetic Interference in *Caenorhabditis elegans*," *Proc. Natl. Acad. Sci. USA*, 95(26):15502-15507 (1998).
Napoli, C. et al., "Introduction of a Chimeric Chalcone Synthase Gene into Petunia Results in Reversible Co-Suppression of Homologous Genes in trans," *The Plant Cell*, 2:279-289 (1990).
Neff, W.E. et al., "Odor Significance of Undersirable Degradation Compounds in Heated Triolein and Trilinolein," *JAOCS*, 77(12):1303-1313 (2000).
Okuley, J., et al., "Arabidopsis FAD2 Gene Encodes the Enzyme That Is Essential for Polyunsaturated Lipid Synthesis," *The Plant Cell*, 6:147-158 (1994).
Padgette et al., "Development, Identification, and Characterization of a Glyphosate-Tolerant Soybean Line," *Crop Sci.*, 35(5):1451-1461 (1995).
Peele et al., "Silencing of a meristematic gene using geminivirus-derived vectors," *The Plant Journal*, 27(4):357-366 (2001).
Pokorný, "Flavor Chemistry of Deep Fat Frying in Oil," *Flavor Chemistry of Lipid Foods* (eds. Min & Smouse), Chapter 7, pp. 113-155, American Oil Chem. Soc., Champaign, IL (1989).
Qing, L., Thesis, "The Isolation and Characterisation of Fatty Acid Desaturase Genes in Cotton," University of Sydney, Australia, pp. ii-iv, 24-26, 121-123, 142, 167-168, 172-174, 179-181 (1998).
Sharp, P.A., "RNA Interference—2001," *Genes & Development*, 15(5):485-490 (2001).
Sharp, P.A., "RNAi and Double-Strand RNA," *Genes & Development*, 13(2):139-141 (1999).
Singh et al., "Metabolic engineering of new fatty acids in plants," *Current Opinion in Plant Biology*, 8(2):197-203 (2005).
Singh et al., "Transgenic expression of a delta 12-epoxygenase gene in Arabidopsis seeds inhibits accumulation of linoleic acid," *Planta*, 212:872-879 (2001).
Smith et al., "Total silencing by intron-spliced hairpin RNAs," *Nature*, 407:319-320 (2000).
Stam et al., "Post-transcriptional silencing of chalcone synthase in *Petunia* by inverted transgene repeats," *The Plant Journal* 12(1):63-82 (1997).
Stam et al., "The Silence of Genes in Transgenic Plants," *Annals of Botany*, 79:3-12 (1997).
Stoutjesdijk et al., "hpRNA-Mediated Targeting of the Arabidopsis FAD 2 Gene Gives Highly Efficient and Stable Silencing," *Plant Physiology*, 129:1723-1731 (2002).
Supplemental European Search Report in European Application No. 03 71 1656.3 completed Jun. 29, 2005.
Supplementary European Search Report European Application No. 04 78 5109 (Nov. 7, 2006).
Supplementary Partial European Search Report in Application No. 03 76 1158 dated Jan. 8, 2007.
Sweetlove et al., "Starch metabolism in tubers of transgenic potato (*Solanum tuberosum*) with increased ADPglycose pyrophosphorylase," *Biochem. J.*, 320:493-498 (1996).
Thomas et al., "Size constraints for targeting post-transcriptional gene silencing and for RNA-directed methylation in *Nicotiana benthamiana* using a potato virus X vector," *The Plant Journal* 25(4):417-25 (2001).
Timmons, J.S. et al., "Relationships Among Dietary Roasted Soybeans, Milk Components, and Spontaneous Oxidized Flavor of Milk", *Journal of Diary Science*, 84(11):2440-2449 (2001).
Toborek, M. et al., "Unsaturated Fatty Acids Selectively Induce an Inflammatory Environment in Human Endothelial Cells", *American Journal of Clinical Nutrition*, 75:119-125 (2002).
van der Krol, A. R. et al., "Flavonoid Genes in Petunia: Addition of a Limited Number of Gene Copies May Lead to a Suppression of Gene Expression", *The Plant Cell*, 2:291-299 (1990).
Voelker et al., *Annu Rev Plant Physiol Plant Mol Biol*, 52:335-361 (2001).

(56) References Cited

OTHER PUBLICATIONS

Warner, K. et al., "Effect of Oleic and Linoleic Acids on the Production of Deep-Fried Odor in Heated Triolein and Trilinolein", *Journal of Agricultural Food Chemical*, 49:899-905 (2001).
Waterhouse, P.M. et al., "Virus Resistance and Gene Silencing in Plants Can be Induced by Simultaneous Expression of Sense and Antisense RNA", *Proc. Natl. Acad. Sci. USA*, 95(23):13959-13964 (1998).
Wesley, S.V. et al., "Construct Design for Efficient, Effective and High-Throughput Gene Silencing in Plants", *The Plant Journal*, 27(6):581-590 (2001).
Yu et al., "RNA interference by expression of short-interfering RNAs and hairpin RNAs in mammalian cells", *Proc. Natl. Acad. Sci.*, 99(9):6047-6052 (2002).
"Food Standards: Australia, New Zealand. Supporting Document 1 (at Approval). Application A1049—Food Derived from Herbicide-Tolerant, High Oleic Acid Soybean Line MON87705. Safety Assessment Report," XP55174211, 38 pages (2011).
Anonymous, "Soybeans A3525," *Asgrow*, pp. 1-2 (2004).
Brace, "Agronomic and seed traits of soybean lines with high-oleate concentration," *Graduate Theses and Dissertations*, Paper 11844 (2010).
Clemente et al., "Soybean Oil: Genetic Approaches for Modification of Functionality and Total Content," *Plant Physiology*, 151:1030-1040 (2009).
La, "Seed Protein, Oil, and Yield of Soybean Genotypes with High and Normal Oleic Acid Concentration," *A Thesis Presented to the Faculty of the Graduate School at the University of Missouri-Columbia*, pp. 1-80 (2013).
Spear, "Agronomic, seed traits and oleate stability of soybean lines containing the high-oleate transgene DP-305423-1 and the molecular characterization of the genomic region flanking the high-oleate transgene," *Graduate Theses and Dissertations*, Paper 12830 (2012).
Search Report completed on Dec. 23, 2013, in ROC (Taiwan) Patent Application No. 098132546.
Holst-Jensen et al., "PCR technology for screening and quantification of genetically modified organisms (GMOs)," *Anal Bioanal Chem.*, 375(8):985-993 (2003).
NCBI GenBank: BH684437.1, *Brassica oleracea* genomic clone BOHXS88TR BO_2_3_KB (2002).
Search Report completed on Sep. 12, 2014, in ROC (Taiwan) Patent Application No. 098132546.

\* cited by examiner

SOYBEAN TRANSGENIC EVENT MON87705 AND METHODS FOR DETECTION THEREOF

CROSS-REFERENCE TO RELATED APPLICATIONS

This application is a divisional of U.S. application Ser. No. 13/670,136, filed Nov. 6, 2012, now U.S. Pat. No. 8,692,080, issued Apr. 8, 2014, which is a divisional of U.S. application Ser. No. 12/568,321, filed Sep. 28, 2009, now U.S. Pat. No. 8,329,989, issued Dec. 11, 2012, which claims the benefit of U.S. Provisional Application Ser. No. 61/100,859, filed on Sep. 29, 2008, all of which are incorporated herein by reference in their entireties.

INCORPORATION OF SEQUENCE LISTING

This application contains an electronic equivalent paper copy of the sequence listing submitted herewith electronically via EFS web and a computer-readable form of the sequence listing submitted herewith electronically via EFS web which contains a file named "56047-0001US_seqlist.txt", which is 50,960 bytes in size (measured in MS-DOS) and which was created on Sep. 8, 2009. The sequence listings submitted herewith as electronic equivalents of a paper copy and computer-readable form are herein incorporated by reference.

FIELD OF THE INVENTION

The present invention relates to transgenic soybean event MON87705 and plant parts and seed thereof. The event exhibits an oil composition comprising altered fatty acid levels. The invention also relates to methods for detecting the presence of soybean event in a biological sample, and provides nucleotide sequences that are capable of doing so.

BACKGROUND OF THE INVENTION

Soybean is an important crop and is a primary food source in many areas of the world. The methods of biotechnology have been applied to soybean for improvement of agronomic traits and the quality of the product. One such quality trait is a soybean oil comprising altered fatty acid levels.

It would be advantageous to be able to detect the presence of transgene/genomic DNA of a particular plant in order to determine whether progeny of a sexual cross contain the transgene/genomic DNA of interest. In addition, a method for detecting a particular plant would be helpful when complying with regulations requiring the pre-market approval and labeling of foods derived from the recombinant crop plants.

Soybean oils have been modified by various breeding methods to create benefits for specific markets. However, a soybean oil that is broadly beneficial to major soybean oil users such as consumers of salad oil, cooking oil and frying oil, and industrial markets such as biodiesel and biolube markets, is not available. Prior soybean oils were either too expensive or lacked an important food quality property such as oxidative stability, good fried food flavor or saturated fat content or an important biodiesel property such as appropriate nitric oxide emissions or cold tolerance or cold flow.

Soybean oil typically contains approximately 20% oleic acid. Oleic acid has one double bond, but is still relatively stable at high temperatures, and oils with high levels of oleic acid are suitable for cooking and other processes where heating is required. Recently, increased consumption of high oleic oils has been recommended, because oleic acid appears to lower blood levels of low density lipoproteins ("LDLs") without affecting levels of high density lipoproteins ("HDLs"). However, some limitation of oleic acid levels is desirable, because when oleic acid is degraded at high temperatures, it creates negative flavor compounds and diminishes the positive flavors created by the oxidation of linoleic acid. Neff et al., JAOCS, 77:1303-1313 (2000); Warner et al., J. Agric. Food Chem. 49:899-905 (2001). It is thus preferable to use oils with oleic acid levels that are 65-85% or less by weight, in order to limit off-flavors in food applications such as frying oil and fried food. Other preferred oils have oleic acid levels that are greater than 55% by weight in order to improve oxidative stability.

For many oil applications, saturated fatty acid levels of less than 8% by weight or even less than about 2-3% by weight are desirable. Soybean oil typically contains about 16-20% saturated fatty acids: 13-16% palmitate and 3-4% stearate (see generally Gunstone et al., The Lipid Handbook, Chapman & Hall, London (1994)). Saturated fatty acids have high melting points which are undesirable in many applications. When used as a feedstock or fuel, saturated fatty acids cause clouding at low temperatures and confer poor cold flow properties such as pour points and cold filter plugging points to the fuel. Oil products containing low saturated fatty acid levels may be preferred by consumers and the food industry because they are perceived as healthier and/or may be labeled as "saturated fat free" in accordance with FDA guidelines. In addition, low saturate oils reduce or eliminate the need to winterize the oil for food applications such as salad oils. In biodiesel and lubricant applications oils with low saturated fatty acid levels confer improved cold flow properties and do not cloud at low temperatures.

Soybean lines that produce seed with mid-oleic and low saturate content would be desirable. Methods disclosed here enable production of soybean seeds that have oleic acid levels in the mid oleic range of 55-80% and saturated fatty acid levels of less than 8%.

The expression of foreign genes in plants is known to be influenced by their chromosomal position, perhaps due to chromatin structure (e.g., heterochromatin) or the proximity of transcriptional regulation elements (e.g., enhancers) close to the integration site (Weising et al., 1988 Ann. Rev. Genet 22:421-477). For this reason, it is often necessary to screen a large number of events in order to identify an event characterized by optimal expression of an introduced gene of interest. For example, it has been observed in plants and in other organisms that there may be wide variation in the levels of expression of an introduced gene among events. There may also be differences in spatial or temporal patterns of expression, for example, differences in the relative expression of a transgene in various plant tissues, that may not correspond to the patterns expected from transcriptional regulatory elements present in the introduced gene construct. For this reason, it is common to produce several hundred to several thousand different events and screen the events for a single event that has the desired transgene expression levels and patterns for commercial purposes. An event that has the desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are suitably adapted to specific local growing conditions.

It is possible to detect the presence of a transgene by any well known nucleic acid detection method such as the polymerase chain reaction (PCR) or DNA hybridization using nucleic acid probes. These detection methods generally focus on frequently used genetic elements, such as promoters, terminators, marker genes, etc. As a result, such methods may not be useful for discriminating between different events, particularly those produced using the same DNA construct unless the sequence of chromosomal DNA adjacent to the inserted DNA ("flanking DNA") is known. An event-specific PCR assay is discussed, for example, by Taverniers et al. (J. Agric. Food Chem., 53: 3041-3052, 2005) in which an event-specific tracing system for transgenic maize lines Bt11, Bt176, and GA21 and for canola event GT73 is demonstrated. In this study, event-specific primers and probes were designed based upon the sequences of the genome/transgene junctions for each event. Transgenic plant event-specific DNA detection methods have also been described in U.S. Pat. Nos. 6,893,826; 6,825,400; 6,740,488; 6,733,974; 6,689,880; 6,900,014 and 6,818,807.

This invention relates to the transgenic soybean (*Glycine max*) plant MON87705 with an oil composition comprising altered fatty acid levels and to the DNA construct of soybean plant MON87705 and the detection of the transgene/genomic insertion region in soybean MON87705 and progeny thereof.

SUMMARY OF THE INVENTION

The present invention includes a transgenic soybean plant designated MON87705 and progeny that are indistinguishable from soybean event MON87705 (to the extent that such progeny also contain at least one allele that corresponds to the inserted transgenic DNA) thereof having seed deposited with American Type Culture Collection (ATCC) with Accession No. PTA-9241. Another aspect of the invention is the progeny plants, or seeds, or regenerable parts of the plants and seeds of the soybean event MON87705. The invention also includes plant parts of the soybean event MON87705 that include, but are not limited to pollen, ovule, flowers, shoots, roots, stems, leaves, pods, seeds and meristematic tissues. Novel genetic compositions contained in the genome of MON87705 and products from MON87705 such as oil, meal, flour, food products, protein supplements and biomasses remaining in a field from which soybean plants corresponding to MON87705 have been harvested are aspects of this invention.

The invention provides a soybean plant capable of producing a seed having an oil composition comprising approximately 55-80% oleic acid by weight and less than 8% saturated fatty acid by weight, wherein genetic determinants for said oil composition is obtainable from soybean having ATCC Accession No. PTA-9241.

According to one aspect of the invention, compositions and methods are provided for detecting the presence of the transgene/genomic insertion region from a novel soybean plant designated MON87705. DNA sequences are provided that comprise at least one junction sequence of MON87705 selected from the group consisting of SEQ ID NO: 1 ([A] corresponding to positions 3449 through 3468 of SEQ ID NO: 6 [F], FIG. 2), SEQ ID NO: 2 ([B] corresponding to positions 10700 through 10719 of SEQ ID NO: 6 [F], FIG. 2) and SEQ ID NO: 18 (corresponding to positions 9266 through 9371 of SEQ ID NO: 6 [F], FIG. 2) and complements thereof wherein a junction sequence is a nucleotide sequence that spans the point at which heterologous DNA inserted into the genome is linked to the soybean cell genomic DNA and detection of this sequence in a biological sample containing soybean DNA is diagnostic for the presence of the soy event MON87705 DNA in said sample (FIG. 2). Such junction sequences can contain at least one of the sequences listed under SEQ ID NO: 1, 2, 18 and the complements thereof. A soybean plant, soybean seed from the plant and progeny of the plant comprising these DNA molecules is an aspect of this invention.

DNA sequences that comprise novel transgene/genomic insertion region, SEQ ID NO: 3 [C], SEQ ID NO: 4 [D] and SEQ ID NO: 5 [E] or SEQ ID NO: 1 [A] and SEQ ID NO: 2 [B] (see FIG. 2) from soybean event MON87705 are aspects of this invention. The soybean plant, seed and progeny comprising these molecules are also aspects of this invention.

According to another aspect of the invention, two DNA molecules are provided for use in a DNA detection method, where the first DNA molecule comprises at least 11 or more, at least 12 or more, or at least 13 or more contiguous polynucleotides of any portion of the transgene region of the DNA molecule of SEQ ID NO: 5 and a DNA molecule of similar length of any portion of a 5' flanking soybean genomic DNA region of SEQ ID NO: 3, where these DNA molecules when used together are useful as DNA primers in a DNA amplification method that produces an amplicon. The amplicon produced using these DNA primers in the DNA amplification method is diagnostic for soybean event MON87705 when the amplicon contains SEQ ID NO: 1. Any amplicon produced by DNA primers homologous or complementary to any portion of SEQ ID NO: 3 and SEQ ID NO: 5, and any amplicon that comprises SEQ ID NO: 1 is an aspect of the invention.

According to another aspect of the invention, two DNA molecules are provided for use in a DNA detection method, wherein the first DNA molecule comprises at least 11 or more contiguous polynucleotides of any portion of the transgene region of the DNA molecule of SEQ ID NO: 5 and a DNA molecule of similar length of any portion of a 3' flanking soybean genomic DNA of SEQ ID NO: 4, where these DNA molecules are useful as DNA primers in a DNA amplification method. The amplicon produced using these DNA primers in the DNA amplification method is diagnostic for soybean event MON87705 when the amplicon contains SEQ ID NO: 2. Any amplicons produced by DNA primers homologous or complementary to any portion of SEQ ID NO: 4 and SEQ ID NO: 5, and any amplicon that comprises SEQ ID NO: 2 is an aspect of the invention.

According to another aspect of the invention, two DNA molecules are provided for use in a DNA detection method, wherein the first DNA molecule comprises at least 11 or more contiguous polynucleotides of any portion of the transgene region of the DNA molecule of SEQ ID NO: 5 or their complements wherein one primer is derived from sequence 5' to SEQ ID NO: 18 and the other primer is derived from sequence 3' to SEQ ID NO: 18 where these DNA molecules are useful as DNA primers in a DNA amplification method. The amplicon produced using these DNA primers in the DNA amplification method is diagnostic for soybean event MON87705 when the amplicon contains SEQ ID NO: 18. Any amplicons produced by DNA primers homologous or complementary to any portion of SEQ ID NO: 5 and any amplicon that comprises SEQ ID NO: 18 is an aspect of the invention.

According to another aspect of the invention, methods of detecting the presence of DNA corresponding to the soybean event MON87705 in a sample are provided. Such methods comprise: (a) contacting the sample comprising DNA with a primer set that, when used in a nucleic acid amplification reaction with genomic DNA from soybean event MON87705, produces an amplicon that is diagnostic for soybean event MON87705; (b) performing a nucleic acid amplification reaction, thereby producing the amplicon; and (c) detecting the amplicon wherein said amplicon comprises one or more or the sequences listed under SEQ ID NOs: 1, 2 and 18.

Another aspect of the invention is a soybean plant, or seed, or product containing the event of the plant or seed of MON87705 wherein the genomic DNA comprises a DNA molecule consisting essentially of the nucleotide sequence of SEQ ID NO: 3 from about positions 1 to 3458, the nucleotide sequence of SEQ ID NO: 5 from about positions 1 to 7251 and the nucleotide sequence of SEQ ID NO: 4 from about positions 1 to 2515 (the contig of which is presented as SEQ ID NO: 6), and complements thereof. A further aspect of the invention is a soybean plant, or seed, or product derived from the plant or seed of MON87705 wherein the genomic DNA comprises a DNA molecule consisting essentially of the nucleotide sequence of SEQ ID NO: 6 from about positions 1 to 13224 and complements thereof. A soybean plant, or seed, or product derived from the plant or seed MON87705, in which the genomic DNA when isolated from the soybean plant, or seed, or product comprises a DNA molecule incorporating SEQ ID NOs: 1, 2 or 18, and complements thereof. In one aspect of the invention, the DNA molecule contains the soybean event MON87705. In another aspect, two copies of the DNA molecule containing the soybean event MON87705 are present in the soybean plant. In another aspect, one copy of the DNA molecule containing the soybean event MON87705 is present in the soybean plant.

Another aspect of the invention is a soybean plant, or seed, or product containing the event of the plant or seed of MON87705, in which the genomic DNA when isolated from the soybean plant, or seed, or product produces an amplicon in a DNA amplification method, where said amplicon comprises at least one sequence from the group consisting of SEQ ID NOs: 1, 2 and 18.

In another aspect, seeds of the soybean plants may be placed in a container. As used herein, a container is any object capable of holding such seeds. A container preferably contains greater than about 500, 1,000, 5,000, or 25,000 seeds where at least about 10%, 25%, 50%, 75% or 100% of the seeds are derived from a plant of the present invention. The present invention also provides a container of over about 10,000, more preferably about 20,000, and even more preferably about 40,000 seeds where over about 10%, more preferably about 25%, more preferably 50% and even more preferably about 75% or 90% of the seeds are seeds derived from a plant of the present invention. The present invention also provides a container of over about 10 kg, more preferably about 25 kg, and even more preferably about 50 kg seeds where over about 10%, more preferably about 25%, more preferably about 50% and even more preferably about 75% or 90% of the seeds are seeds derived from a plant of the present invention.

Another aspect of the invention provides a method for detecting the presence or absence of soybean transgenic event MON87705 in a biological sample comprising a) extracting DNA from said sample; and b) assaying the presence or absence of a polynucleotide having a sequence corresponding to that shown under SEQ ID NOs: 1, 2 or 18, whereby the presence or absence of soybean event MON87705 in said sample can be ascertained.

According to another aspect of the invention, methods of detecting the presence of DNA corresponding to the MON87705 event in a sample, comprising: (a) contacting the sample with a probe that hybridizes under stringent hybridization conditions with a sequence selected from the group consisting of SEQ ID NO: 1 and SEQ ID NO: 2, and their complements, and does not hybridize under the stringent hybridization conditions with soybean plant DNA that does not comprise SEQ ID NO: 1 and SEQ ID NO: 2; (b) subjecting the sample and probe to stringent hybridization conditions; and (c) detecting binding of the probe to said sample; wherein binding is diagnostic for the presence of said DNA in said sample. Another aspect of the invention is a probe comprising from about 11- to about 20 consecutive nucleotides in length for use in detecting the presence of soybean event MON87705 in a biological sample, wherein said consecutive nucleotides are selected from the group consisting of SEQ ID NO: 1 and SEQ ID NO: 2, and their complements. The probe may be a deoxyribonucleic acid, a ribonucleic acid or a nucleotide analogue. The probe may be labeled with at least one fluorophore.

Another aspect of the invention is a method of determining zygosity of the progeny of soybean event MON87705, the method comprising (a) contacting the sample comprising soybean DNA with the primer set SQ21928 (SEQ ID NO: 11), SQ20901 (SEQ ID NO: 12), and the probe 6FAM™-labeled PB10164 (SEQ ID NO: 13) and that when used in a nucleic-acid amplification reaction with genomic DNA from soybean event MON87705, produces a first amplicon, releasing a fluorescent signal from the combination of primers SQ21928 and SQ20901 and a 6FAM™-labeled primer/probe, PB10164 that is diagnostic for soybean event MON87705 (b) performing a nucleic acid amplification reaction, thereby producing the first amplicon; and (c) detecting said first amplicon; and (d) contacting the sample comprising soybean DNA with the primer set, SQ21928 (SEQ ID NO: 11) and SQ21905 (SEQ ID NO: 15), and a VIC™-labeled PB10335 (SEQ ID NO: 14) that when used in a nucleic-acid amplification reaction with genomic DNA from soybean plants produces a second amplicon, releasing a fluorescent signal that is diagnostic of the wild-type soybean genomic DNA homologous to the soybean genomic region of a transgene insertion identified as soybean event MON87705; (e) performing a nucleic acid amplification reaction, thereby producing the second amplicon and (f) detecting said second amplicon; and (g) comparing the first and second amplicons in a sample, wherein the presence of both amplicons indicates the sample is heterozygous for the transgene insertion.

Another aspect of the invention is a method of determining zygosity of the progeny of soybean event MON87705, the method comprising (a) contacting the sample comprising soybean DNA with the primer set SQ21928 (SEQ ID NO: 11), SQ20901 (SEQ ID NO: 12), and SQ21905 (SEQ ID NO: 15), that when used in a nucleic-acid amplification reaction with genomic DNA from soybean event MON87705, produces a first amplicon from the combination of primers SQ21928 and SQ20901 that is diagnostic for soybean event MON87705 (b) performing a nucleic acid amplification reaction, thereby producing the first amplicon; and (c) detecting said first amplicon; and (d) contacting the sample comprising soybean DNA with the primer set, SQ21928 and SQ21905, that when used in a nucleic-acid amplification reaction with genomic DNA from soybean plants produces a second amplicon from the combination of primers SQ21928 and SQ21905 that is diagnostic of the wild-type soybean genomic DNA homologous to the soybean genomic region of a transgene insertion identified as soybean event MON87705; (e) performing a nucleic acid amplification reaction, thereby producing the second amplicon and (f) detecting said second amplicon; and (g) comparing the first and second amplicons in a sample, wherein the presence of both amplicons indicates the sample is heterozygous for the transgene insertion.

The invention also provides a composition having a DNA molecule selected from the group consisting of SEQ ID NOs: 1, 2 and 18, wherein said composition is a commodity product selected from the group consisting of soybean meal, soy flour, soy protein concentrate, soy protein isolates, texturized soy protein concentrate, hydrolyzed soy protein and whipped topping.

Another aspect of the invention is a method for detecting the presence of a nucleotide sequence diagnostic for the presence of soybean event MON87705 in a biological sample, comprising detecting the presence of a nucleotide sequence wherein said sequence is selected from the group consisting of SEQ ID NOs: 1, 2 and 18, wherein said biological sample is selected from the group consisting of soybean meal, soy flour, soy protein concentrate, soy protein isolates, texturized soy protein concentrate, hydrolyzed soy protein and whipped topping.

Kits for the detection of soybean event MON87705 in a soybean sample are provided that comprise nucleotide components designed based on detecting one or more sequences shown under SEQ ID NOs: 1, 2 and 18. Kits for the detection of soybean event MON87705 are provided which use primers designed from SEQ ID NO: 3, 4 or 5. An amplicon produced using said kit is diagnostic for MON87705 when the amplicon contains one or more nucleotide sequences listed under SEQ ID NOs: 1, 2 and 18.

Another aspect of the invention is a method for producing a soybean plant comprising altered fatty acid levels, comprising crossing a plant comprising soybean event MON87705 with a soybean plant lacking soybean event MON87705 to obtain a plant comprising said soybean event MON87705 and altered fatty acid levels, wherein a representative sample of seed comprising said event was deposited under ATCC Accession No. PTA-9241.

Also provided is a method of producing a soybean variety comprising soybean event MON87705, comprising backcrossing soybean event MON87769 into said variety, wherein a representative sample of seed comprising said event was deposited under ATCC Accession No. PTA-9241.

Another aspect of the invention is a soybean plant capable of producing seeds having an oil composition comprising approx. 55-80% oleic acid and less than 8% saturated fatty acid, wherein genetic determinants for said oil composition is obtainable from soybean having ATCC Accession No. PTA-9241. Also provided is an oil composition obtained from seeds of the soybean plant and a commodity product derived from the oil selected from the group consisting of cooking oil, salad oil, shortening, lecithin, nontoxic plastics, printing inks, lubricants, waxes, hydraulic fluids, electric transformer fluids, solvents, cosmetics, hair care products and biodiesel.

An oil of the present invention may be blended with other oils. In one aspect, the oil produced from plants of the present invention or generated by a method of the present invention constitutes greater than 0.5%, 1%, 5%, 10%, 25%, 50%, 75% or 90% by volume or weight of the oil component of any product. In another aspect, the oil preparation may be blended and can constitute greater than 10%, 25%, 35%, 50% or 75% of the blend by volume. Oil produced from a plant of the present invention can be admixed with one or more organic solvents or petroleum distillates.

A further aspect of the invention is a genome of a soybean cell comprising a polynucleotide having a sequence selected from the group consisting of sequences listed under SEQ ID NO: 1, 2 and 18.

Another aspect of the invention is a soybean plant, or seed, or seed progeny, or product derived from the plant or seed of MON87705. Seed for sale for planting or for making commodity products is an aspect of the invention. Such commodity products include, but are not limited to, whole or processed soy seeds, animal feed, vegetable oil, meal, flour, nontoxic plastics, printing inks, lubricants, waxes, hydraulic fluids, electric transformer fluids, solvents, cosmetics, hair care products, soymilk, soy nut butter, natto, tempeh, soy protein concentrate, soy protein isolates, texturized soy protein concentrate, hydrolyzed soy protein, whipped topping, cooking oil, salad oil, shortening, lecithin, edible whole soybeans (raw, roasted, or as edamame), soymilk, soy yogurt, soy cheese, tofu, yuba and biodiesel.

The foregoing and other aspects of the invention will become more apparent from the following detailed description.

BRIEF DESCRIPTION OF THE SEQUENCES

Figure 1:
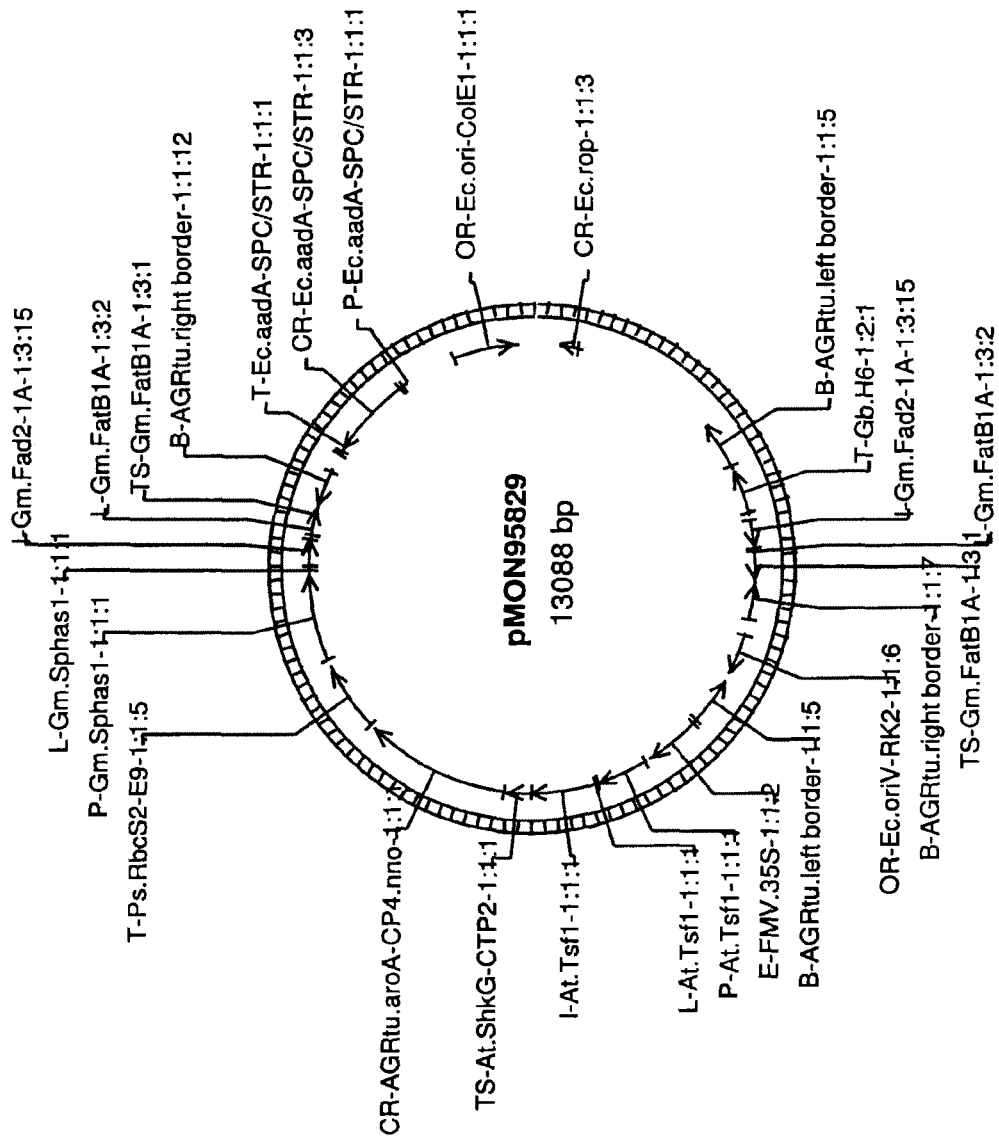
FIG. 1. Map of binary transformation vector, pMON95829 that was used to generate soybean plant MON87705.

SEQ ID NO: 1—A 20 nucleotide sequence representing the 5' left border junction between the soybean genomic DNA and the integrated T-DNA. This sequence corresponds to positions 3413 to 3432 of SEQ ID NO: 6. In addition, SEQ ID NO: 1 ([A] of FIG. 2) is a nucleotide sequence corresponding to positions 3432 through 3422 of SEQ ID NO: 3 ([C], see FIG. 2) and the integrated 5' left border of the integrated T-DNA corresponding to positions 1 through 10 of SEQ ID NO: 5 ([E], see FIG. 2).

SEQ ID NO: 2—A 20 nucleotide sequence representing the 3' left border junction between the integrated T-DNA and the soybean genomic DNA. This sequence corresponds to positions 10664 to 10683 of SEQ ID NO: 6. In addition, SEQ ID NO: 2 ([B], see FIG. 2) is a nucleotide sequence corresponding positions 7242 through 7251 of SEQ ID NO: 5 ([E], see FIG. 2) and the 3' flanking sequence corresponding to positions 1 through 10 of SEQ ID NO: 4 ([D], see FIG. 2).

SEQ ID NO: 3—The 5' sequence flanking the inserted DNA of MON87705 up to the T-DNA insertion.

SEQ ID NO: 4—The 3' sequence flanking the inserted DNA of MON87705 up to the T-DNA insertion.

SEQ ID NO: 5—The sequence of the inserted T-DNAs, including residual border sequence after integration.

SEQ ID NO: 6—A 13188 bp nucleotide sequence representing the contig of the 5' sequence flanking the inserted DNA of MON87705 (SEQ ID NO: 3), the sequence of the integrated expression cassette (SEQ ID NO: 5) and the 3' sequence flanking the inserted DNA of MON87705 (SEQ ID NO: 4).

SEQ ID NO: 7—A 6583 bp nucleotide sequence representing the aroA-CP4 expression cassette and the FAD2-1A/FATB suppression cassette as assembled in MON87705 from the co-integration of the pMON95829 T-DNAs.

SEQ ID NO: 8—Primer SQ20129 used to identify the MON87705 event. Primer SQ20129 corresponds to a region in the 3' of the inserted T-DNA close to the 3' left border corresponding to positions 10645 to 10663 of SEQ ID NO: 6. A PCR amplicon produced using the combination of primers SQ20129 and SQ20130 is positive for the presence of the event MON87705.

SEQ ID NO: 9—Primer SQ20130 used to identify the MON87705. Primer SQ20130 is complimentary to the region 3' of the T-DNA insertion border corresponding to positions 10688 to 10707 of SEQ ID NO: 6. A PCR amplicon produced using the combination of primers SQ20129 and SQ20130 is positive for the presence of the event MON87705.

SEQ ID NO: 10—Probe PB10043 used to identify the MON87705 event. This probe is a 6FAM™-labeled synthetic oligonucleotide whose sequence corresponds to positions 10666 to 10686 of SEQ ID NO: 6. Release of a fluorescent signal in an amplification reaction using primers SQ20129 and SQ20130 in combination with 6FAM™-labeled probe PB10043 is diagnostic of event MON87705.

SEQ ID NO: 11—Primer SQ21928 used to identify the MON87705 event. Primer SQ21928 is complimentary to the region 3' of the T-DNA insertion border corresponding to positions 10675 to 10699 of SEQ ID NO: 6. A PCR amplicon produced using the combination of primers SQ20901 and SQ21928 is positive for the presence of the event MON87705. Primer SQ21928 is also used to determine zygosity of MON87705 events. Detection of a PCR amplicon and the release of fluorescent signal using 6FAM™-labeled Probe PB10335 and primers SQ21928 and SQ21905 is positive for presence of wild type in a zygosity assay. Eighteen base pairs of the sequence corresponds to positions 1053 to 1070 of SEQ ID NO: 6 with the remaining seven base pairs corresponding to seven base pairs in the forty base pair region of wild type sequence shown as SEQ ID NO: 17 which was lost in the generation of the MON87705 event.

SEQ ID NO: 12—Primer SQ20901 used to identify the MON87705 event. Primer SQ20901 corresponds to a region in the 3' of the inserted T-DNA close to the 3' left border corresponding to positions 10624 to 10647 of SEQ ID NO: 6. A PCR amplicon produced from the combination of primers SQ21928 and SQ20901 is positive for the presence of the event MON87705.

SEQ ID NO: 13—Probe PB10164 used to identify the MON87705 event. This probe is a 6FAM™-labeled synthetic oligonucleotide whose sequence corresponds to positions 10651 to 10670 of SEQ ID NO: 6. Release of a fluorescent signal in an amplification reaction using primers SQ21928 and SQ20901 in combination with 6FAM™-labeled probe PB10164 is diagnostic of event MON87705.

SEQ ID NO: 14—Probe PB10335 used to determine zygosity of MON87705 events. This probe is a VIC™-labeled synthetic oligonucloetide whose sequence corresponds to a region of the wild-type genomic DNA. A PCR amplicon produced using primers SQ21928 and SQ21905 causes the release of a fluorescent signal using probe PB10335 which is positive for the presence of the wild-type allele in a zygosity assay for event MON87705. This sequence corresponds to positions 12 to 31 of the forty base pair wild type sequence listed as SEQ ID NO: 17 which was lost in the generation of the MON87705 event.

SEQ ID NO: 15—Primer SQ21905 used to determine zygosity of MON87705 events. Detection of a PCR amplicon using 6FAM™-labeled Probe PB10335 and primers SQ21928 and SQ21905 is positive for presence of wild type in a zygosity assay. Sixteen base pairs of sequence corresponds to positions 1037 to 1052 of SEQ ID NO: 6 while this primer continues ten base pairs into the forty base pair region of wild type sequence listed as SEQ ID NO: 16 which was lost in the generation of the MON87705 event.

SEQ ID NO: 16—Forty base pair sequence that was lost at the junction of the tandem repeat sequence (SEQ ID NO: 17) and the 5' genomic sequences. This sequence is found in the wild type and would have been located between base pair 1052 and 1053 in SEQ ID NO: 6 had it not been lost during the generation of the MON87705 event. Due to the duplication of the genomic sequence upon the generation of the MON87705 event, the terminal twelve bases of sequence is also located at position 10670 to 10681 of SEQ ID NO: 6, but the remaining twenty eight base pairs are completely absent from the MON87705 event and therefore may be utilized to identify the wild type in an assay for zygosity.

SEQ ID NO: 17—This 2370 bp sequence is the portion of the wild type genomic sequences which was apparently duplicated upon generation of the MON87705 event. This region of duplication corresponds to position 1053 to 3422 and is nearly identical to position 10682 to 13051 of SEQ ID NO: 6. Duplicate Genomewalker™ based clones of this region shared two mismatches in the repeat located on the 5' end of the insert when compared to the 3' end and the soy genomic sequence. The two altered bases in the 5' repeat, along with the deletion found on the 5' end of the duplication (SEQ ID NO:16) leads us to the additional that the tandem sequences corresponding to position 1053 to 3422 is the newly generated sequence while the sequence corresponding to position 10682 to 13051 is the original wild type sequence.

SEQ ID NO: 18—This 106 bp sequence spans the right border to right border junction generated upon the co-integration of the two pMON95829 T-DNAs to yield event MON87705. It starts and ends with twenty bases of the suppression target FATB, one from each arm of the inverted repeat, and contains residual border sequences and inserted sequences generated in the integration of the sequences found in the MON87705 event. This sequence corresponds to position 9230 to 9335 of SEQ ID NO: 6. Although this sequence lies within the suppression cassette, due to the random nature of the assembly of the two T-DNAs in vivo, the sequence combination is unique to the MON87705 event.

SEQ ID NO: 19—Primer 24894 used in the secondary (nested) PCR in combination with AP2 for amplification of the Genomewalker™-derived 5' flank extension. This sequence corresponds to position 3722 to 3748 of SEQ ID NO: 6.

SEQ ID NO: 20—Primer 24895 used in the primary PCR in combination with AP1 for amplification of the Genomewalker™-derived 5' flank extension. This sequence corresponds to position 3798 to 3827 of SEQ ID NO: 6.

DETAILED DESCRIPTION

The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., *Glossary of Genetics: Classical and Molecular*, 5th edition, Springer-Verlag: New York, 1991; and Lewin, *Genes V*, Oxford University Press: New York, 1994.

As used herein, the term "soybean" means *Glyycine max* and includes all plant varieties that can be bred with soybean, including wild soybean species as well as those plants belonging to *Glycine soja* that permit breeding between species.

"Glyphosate" refers to N-phosphonomethylglycine and its salts. N-phosphonomethylglycine is a well-known herbicide that has activity on a broad spectrum of plant species.

"Desaturase" refers to a polypeptide that can desaturate or catalyze formation of a double bond between consecutive carbons of one or more fatty acids to produce a mono- or poly-unsaturated fatty acid or a precursor thereof. Of particular interest are polypeptides that can catalyze the conversion of oleic acid to linoleic acid or linoleic acid to α-linolenic acid, which includes enzymes which desaturate at the 12 or 15 positions. Considerations for choosing a specific polypeptide having desaturase activity include, but are not limited to, the pH optimum of the polypeptide, whether the polypeptide is a rate limiting enzyme or a component thereof, whether the desaturase used is essential for synthesis of a desired PUFA, and/or whether a co-factor is required by the polypeptide. The expressed polypeptide preferably has characteristics that are compatible with the biochemical environment of its location in the host cell. For example, the polypeptide may have to compete for substrate(s). An endogenous desaturase may also be the target of gene suppression.

"Thioesterase" refers to a polypeptide that can hydrolyze the thioester bond of molecules (splitting of an ester bond into acid and alcohol, in the presence of water) specifically at a thiol group. Of particular interest are polypeptides that can catalyze the hydrolysis of the thioester bond contained in acyl-acyl-carrier proteins (acyl-ACP), especially stearoyl- and palmitoyl-ACP substrates. Such hydrolysis produces a free fatty acid and ACP, thereby terminating the fatty acid biosynthesis of plants located in the plastid and readies the fatty acid for export to the cytoplasm. Considerations for choosing a specific polypeptide having thioesterase activity include, but are not limited to, the pH optimum of the polypeptide, whether the polypeptide is a rate limiting enzyme or a component thereof and whether the thioesterase used is essential for increased production of saturated fatty acids. The expressed polypeptide preferably has characteristics that are compatible with the biochemical environment of its location in the host cell. For example, the polypeptide may have to compete for substrate(s). An endogenous thioesterase may also be the target of gene suppression.

A "commodity product" refers to any product which is comprised of material derived from soybean or soybean oil and is sold to consumers. Processed soybeans are the largest source of protein feed and vegetable oil in the world. The soybean plant MON87705 can be used to manufacture commodities typically acquired from soy. Soybeans of MON87705 can be processed into meal, flour, or oil as well as be used as a protein or oil source in animal feeds for both terrestrial and aquatic animals. Soybeans and soybean oils from MON87705 can be used in the manufacture of many different products, not limited to, nontoxic plastics, printing inks, lubricants, waxes, hydraulic fluids, electric transformer fluids, solvents, cosmetics, and hair care products. Soybeans and oils of MON87705 can be suitable for use in a variety of soyfoods made from whole soybeans, such as soymilk, soy nut butter, natto, and tempeh, and soyfoods made from processed soybeans and soybean oil, including soybean meal, soy flour, soy protein concentrate, soy protein isolates, texturized soy protein concentrate, hydrolyzed soy protein, whipped topping, cooking oil, salad oil, shortening, and lecithin. Whole soybeans are also edible, and are typically sold to consumers raw, roasted, or as edamamé. Soymilk, which is typically produced by soaking and grinding whole soybeans, may be consumed without other processing, spray-dried, or processed to form soy yogurt, soy cheese, tofu, or yuba.

Oils of MON87705 can be used to make biodiesel. The use of biodiesel in conventional diesel engines results in substantial reductions of pollutants such as sulfates, carbon monoxide, and particulates compared to petroleum diesel fuel, and use in school buses can greatly reduce exposure to toxic diesel exhaust. Biodiesel is typically obtained by extracting, filtering and refining soybean oil to remove free fats and phospholipids, and then transesterifying the oil with methanol to form methyl esters of the fatty acids (see for example U.S. Pat. No. 5,891,203). The resultant soy methyl esters are commonly referred to as "biodiesel." The oil derived from MON87705 may also be used as a diesel fuel without the formation of methyl esters, such as, for example, by mixing acetals with the oil (see for example U.S. Pat. No. 6,013,114). The seeds of MON87705 used to make said oils can be identified by the methods of the present invention. It is expected that purified oil from MON87705 event seeds or mixtures of seeds some or all of which are MON87705 will have relatively no DNA available for testing. However, the seeds from which the oils are extracted can be characterized with the method of the present invention to identify the presence of the MON87705 event within the population of seeds used to make said oils. Also, plant waste from the process used to make said oils can be used in the methods of the present invention to identify the presence of MON87705 events within a mixture of seeds processed to make said oils. Likewise, plant debris left after making a commodity product, or left behind following harvest of the soybean seed, can be characterized by the methods of the present invention to identify MON87705 events within the raw materials used to make said commodity products.

The present invention also includes a blended or non-blended soybean oil of MON87705. Such oil may be blended with other oils. In a preferred embodiment, the oil produced from plants of the present invention or generated by a method of the present invention constitutes greater than 0.5%, 1%, 5%, 10%, 25%, 50%, 75% or 90% by volume or weight of the oil component of any product. In another embodiment, the oil preparation may be blended and can constitute greater than 10%, 25%, 35%, 50% or 75% of the blend by volume. Oil produced from a plant of the present invention can be admixed with one or more organic solvents or petroleum distillates.

A transgenic "event" is produced by transformation of plant cells with heterologous DNA, i.e., a nucleic acid construct that includes a transgene of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety, wherein the progeny comprises the heterologous DNA. Even after repeated back-crossing to a recurrent parent, the inserted DNA and flanking DNA from the original transformation may be present in the progeny of the cross at the same chromosomal location. The term "event" also refers to DNA from the original transformant comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA. The present invention relates to the event MON87705 DNA, plant cells, tissues, seeds and processed products derived from MON87705.

It is also to be understood that two different transgenic plants, or a transgenic plant and a wild-type plant, can also be mated to produce offspring that contain two independently segregating added, exogenous genes. The offspring can be homozygous or heterozygous for the genes. Selfing of appropriate progeny can produce plants that are homozygous for both added, exogenous genes. Back-crossing to a parental plant and out-crossing with a non-transgenic plant are also contemplated, as is vegetative propagation. Descriptions of other breeding methods that are commonly used for different traits and crops can be found in one of several references, e.g., Fehr, in *Breeding Methods for Cultivar Development*, Wilcox J. ed., American Society of Agronomy, Madison Wis. (1987).

As used herein when referring to an "isolated DNA molecule", it is intended that the DNA molecule be one that is present, alone or in combination with other compositions, but not within its natural environment. For example, a coding sequence, intron sequence, untranslated leader sequence, promoter sequence, transcriptional termination sequence, and the like, that are naturally found within the DNA of a soybean genome are not considered to be isolated from the soybean genome so long as they are within the soybean genome. However, each of these components, and subparts of these components, would be "isolated" within the scope of this disclosure so long as the structures and components are not within the soybean genome. For the purposes of this disclosure, any transgenic nucleotide sequence, i.e., the nucleotide sequence of the DNA inserted into the genome of the cells of the soybean plant event MON87705 would be considered to be an isolated nucleotide sequence whether it is present within the plasmid used to transform soybean cells from which the MON87705 event arose, within the genome of the event MON87705, present in detectable amounts in tissues, progeny, biological samples or commodity products derived from the event MON87705. The nucleotide sequence or any fragment derived therefrom would therefore be considered to be isolated or isolatable if the DNA molecule can be extracted from cells, or tissues, or homogenate from a plant or seed or plant organ; or can be produced as an amplicon from extracted DNA or RNA from cells, or tissues, or homogenate from a plant or seed or plant organ, any of which is derived from such materials derived from the event MON87705. For that matter, the junction sequences as set forth at SEQ ID NOs: 1, 2 and 18, and nucleotide sequences derived from event MON87705 that also contain these junction sequences are considered to be isolated or isolatable, whether these sequences are present within the genome of the cells of event MON87705 or present in detectable amounts in tissues, progeny, biological samples or commodity products derived from the event MON87705.

A DNA molecule of the present invention may also be a recombinant DNA molecule. As used herein, the term recombinant means any agent (e.g. DNA, peptide etc.), that is, or results, however indirect, from human manipulation of a nucleic acid molecule.

A "probe" is an isolated nucleic acid to which is attached a conventional detectable label or reporter molecule, e.g., a radioactive isotope, ligand, chemiluminescent agent, or enzyme. Such a probe is complementary to a strand of a target nucleic acid, in the case of the present invention, to a strand of genomic DNA from soybean event MON87705 whether from a soybean plant or from a sample that includes DNA from the event. Probes according to the present invention include not only deoxyribonucleic or ribonucleic acids but also polyamides and other probe materials that bind specifically to a target DNA sequence and such binding can be used to detect the presence of that target DNA sequence.

"Primers" are isolated nucleic acids that are annealed to a complementary target DNA strand by nucleic acid hybridization to form a hybrid between the primer and the target DNA strand, and then extended along the target DNA strand by a polymerase, e.g., a DNA polymerase. Primer pairs of the present invention refer to their use for amplification of a target nucleic acid sequence, e.g., by the polymerase chain reaction (PCR) or other conventional nucleic-acid amplification methods.

Probes and primers are generally 11 nucleotides or more in length, preferably 15 nucleotides or more, more preferably 18 nucleotides or more, more preferably 20 nucleotides or more, more preferably 24 nucleotides or more, and most preferably 30 nucleotides or more. Such probes and primers hybridize specifically to a target sequence under high stringency hybridization conditions. Preferably, probes and primers according to the present invention have complete sequence similarity with the target sequence, although probes differing from the target sequence and that retain the ability to hybridize to target sequences may be designed by conventional methods.

Methods for preparing and using probes and primers are described, for example, in *Molecular Cloning: A Laboratory Manual*, 2nd ed., vol. 1-3, ed. Sambrook et al., Cold Spring Harbor Laboratory Press, Cold Spring Harbor, N.Y., 1989 (hereinafter, "Sambrook et al., 1989"); *Current Protocols in Molecular Biology*, ed. Ausubel et al., Greene Publishing and Wiley-Interscience, New York, 1992 (with periodic updates) (hereinafter, "Ausubel et al., 1992"); and Innis et al., *PCR Protocols: A Guide to Methods and Applications*, Academic Press: San Diego, 1990. PCR-primer pairs can be derived from a known sequence, for example, by using computer programs intended for that purpose such as Primer (Version 0.5, © 1991, Whitehead Institute for Biomedical Research, Cambridge, Mass.).

Primers and probes based on the flanking DNA and insert sequences disclosed herein can be used to confirm (and, if necessary, to correct) the disclosed sequences by conventional methods, e.g., by re-cloning and sequencing such sequences.

The nucleic acid probes and primers of the present invention hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989, and by Haymes et al., In: *Nucleic Acid Hybridization, A Practical Approach*, IRL Press, Washington, D.C. (1985). Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. In a embodiment, a nucleic acid of the present invention will specifically hybridize to one or more of the nucleic acid molecules set forth in SEQ ID NO: 1 and 2 or complements thereof or fragments of either under moderately stringent conditions, for example at about 2.0×SSC and about 65° C. In a particularly preferred embodiment, a nucleic acid of the present invention will specifically hybridize to one or more of the nucleic acid molecules set forth in SEQ ID NO:1 and SEQ ID NO: 2 or complements or fragments of either under high stringency conditions. In one aspect of the present invention, a marker nucleic acid molecule of the present invention has the nucleic acid sequence set forth in SEQ ID NO: 1 and SEQ ID NO: 2 or complements thereof or fragments of either. In another aspect of the present invention, a marker nucleic acid molecule of the present invention shares 80%, 81%, 82%, 83%, 84%, 85%, 86%, 87%, 88%, 89%, 90%, 912%, 92%, 93%, 94%, 95%, 96%, 97%, 98%, 99% and 100% sequence identity with the nucleic acid sequence set forth in SEQ ID NO: 1 and SEQ ID NO: 2 or complement thereof or fragments of either. In a further aspect of the present invention, a marker nucleic acid molecule of the present invention shares 95% 96%, 97%, 98%, 99% and 100% sequence identity with the sequence set forth in SEQ ID NO: 1 and SEQ ID NO: 2 or complement thereof or fragments of either. SEQ ID NO: 1 and SEQ ID NO: 2 may be used as markers in plant breeding methods to identify the progeny of genetic crosses similar to the methods described for simple sequence repeat DNA marker analysis, in "DNA markers: Protocols, applications, and overviews: (1997) 173-185, Cregan, et al., eds., Wiley-Liss NY; all of which is herein incorporated by reference. The hybridization of the probe to the target DNA molecule can be detected by any number of methods known to those skilled in the art, these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon, in a DNA thermal amplification reaction.

The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic-acid amplification of a target nucleic acid sequence that is part of a nucleic acid template. For example, to determine whether the soybean plant resulting from a sexual cross contains transgenic event genomic DNA from the soybean plant of the present invention, DNA extracted from a soybean plant tissue sample may be subjected to nucleic acid amplification method using a primer pair that includes a primer derived from flanking sequence in the genome of the plant adjacent to the insertion site of inserted heterologous DNA, and a second primer derived from the inserted heterologous DNA to produce an amplicon that is diagnostic for the presence of the event DNA. The amplicon is of a length and has a sequence that is also diagnostic for the event. The amplicon may range in length from the combined length of the primer pairs plus one nucleotide base pair, preferably plus about fifty nucleotide base pairs, more preferably plus about two hundred-fifty nucleotide base pairs, and even more preferably plus about four hundred-fifty nucleotide base pairs. Alternatively, a primer pair can be derived from flanking sequence on both sides of the inserted DNA so as to produce an amplicon that includes the entire insert nucleotide sequence. A member of a primer pair derived from the plant genomic sequence may be located a distance from the inserted DNA molecule, this distance can range from one nucleotide base pair up to about twenty thousand nucleotide base pairs. The use of the term "amplicon" specifically excludes primer-dimers that may be formed in the DNA thermal amplification reaction.

Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202 and in PCR Protocols: A Guide to Methods and Applications, ed. Innis et al., Academic Press, San Diego, 1990. PCR amplification methods have been developed to amplify up to 22 kb of genomic DNA and up to 42 kb of bacteriophage DNA (Cheng et al., Proc. Natl. Acad. Sci. USA 91:5695-5699, 1994). These methods as well as other methods known in the art of DNA amplification may be used in the practice of the present invention. The sequence of the heterologous DNA insert or flanking sequence from soybean event MON87705 with seed samples deposited as ATCC PTA-9241 can be verified (and corrected if necessary) by amplifying such sequences from the event using primers derived from the sequences provided herein followed by standard DNA sequencing of the PCR amplicon or of the cloned DNA.

The amplicon produced by these methods may be detected by a plurality of techniques. One such method is Genetic Bit Analysis (Nikiforov, et al. Nucleic Acid Res. 22:4167-4175, 1994) where an DNA oligonucleotide is designed which overlaps both the adjacent flanking genomic DNA sequence and the inserted DNA sequence. The oligonucleotide is immobilized in wells of a microwell plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labelled ddNTPs specific for the expected next base. Readout may be fluorescent or ELISA-based. A signal indicates presence of the insert/flanking sequence due to successful amplification, hybridization, and single base extension.

Another method is the Pyrosequencing technique as described by Winge (Innov. Pharma. Tech. 00:18-24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. dNTPs are added individually and the incorporation results in a light signal which is measured. A light signal indicates the presence of the transgene insert/flanking sequence due to successful amplification, hybridization, and single or multi-base extension.

Fluorescence Polarization as described by Chen, et al., (Genome Res. 9:492-498, 1999) is a method that can be used to detect the amplicon of the present invention. Using this method an oligonucleotide is designed which overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

TaqMan® (PE Applied Biosystems, Foster City, Calif.) is described as a method of detecting and quantifying the presence of a DNA sequence and is fully understood in the instructions provided by the manufacturer. Briefly, a FRET oligonucleotide probe is designed which overlaps the genomic flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

Molecular Beacons have been described for use in sequence detection as described in Tyangi, et al. (Nature Biotech. 14:303-308, 1996) Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties that results in the production of a fluorescent signal. The fluorescent signal indicates the presence of the flanking/transgene insert sequence due to successful amplification and hybridization.

Other described methods, such as microfluidics (US Patent Pub. 2006068398, U.S. Pat. No. 6,544,734) provide methods and devices to separate and amplify DNA samples. Optical dyes are used to detect and quantitate specific DNA molecules (WO/05017181). Nanotube devices (WO/06024023) that comprise an electronic sensor for the detection of DNA molecules or nanobeads that bind specific DNA molecules and can then be detected.

Figure 2:
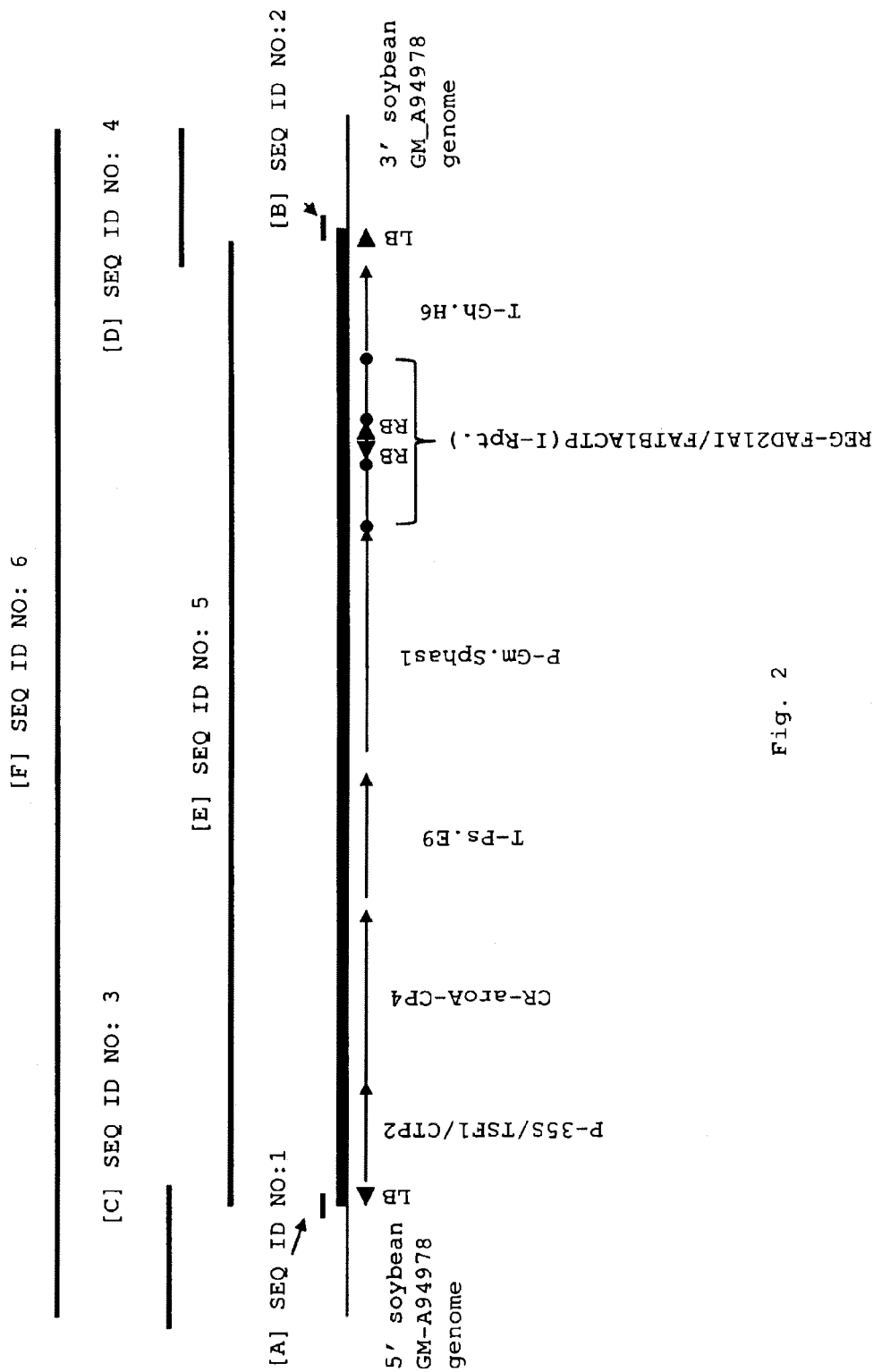
FIG. 2. Organization of the transgenic insert in the genome of soybean event MON87705; [A] corresponds to the relative position of SEQ ID NO: 1 which forms the junction between SEQ ID NO: 3 and SEQ ID NO: 5; [B] corresponds to the relative position of SEQ ID NO: 2 which forms the junction between SEQ ID NO: 4 and SEQ ID NO: 5; [C] corresponds to the relative position of SEQ ID NO: 3, the soybean genome sequence flanking the arbitrarily assigned/designated 5' end of the expression cassette integrated into the genome in event MON87705; [D] corresponds to the relative position of SEQ ID NO: 4, the soybean genome sequence flanking the arbitrarily assigned/designated 3' end of the expression cassette integrated into the genome in event MON87705; [E] represents the various elements comprising SEQ ID NO: 5 and is the sequence of the expression cassette inserted into the genome of the event MON87705; and [F] represents the contiguous sequence comprising, as represented in the figure from left to right, SEQ ID NO:3, SEQ ID NO:5 and SEQ ID NO:4, in which SEQ ID NO:1 and SEQ ID NO:2 are incorporated as set forth above, as these sequences are present in the genome in event MON87705.

DNA detection kits can be developed using the compositions disclosed herein and the methods well known in the art of DNA detection. The kits are useful for the identification of soybean event MON87705 DNA in a sample and can be applied to methods for breeding soybean plants containing the appropriate event DNA. The kits may contain DNA primers or probes that are homologous or complementary to SEQ ID NO: 1 through SEQ ID NO: 5 or DNA primers or probes homologous or complementary to DNA contained in the transgene genetic elements of DNA. These DNA sequences can be used in DNA amplification reactions or as probes in a DNA hybridization method. The sequences of the genomic DNA and transgene genetic elements contained in MON87705 soybean genome are illustrated in FIG. 2; the transgene genetic element contained in the T-DNAs are organized as follows: the first T-DNA begins with the octopine left border sequence, followed by the first artificial gene comprised of the 35S enhancer from figwort mosaic virus (FMV), and promoter, intron, and leader sequence from the *Arabidopsis thaliana* Tsf1 gene, which is upstream of the ShkG transit peptide fused to an optimized aroA-CP4, which is upstream of the 3' UTR of the RbcS2 (E9) gene from *Pisum sativum*, followed by the second cassette which is comprised of the promoter and leader sequence from the *Glycine max* 7S alpha prime subunit of beta-conglycinin gene, which is upstream of the sense half of the inverted repeat containing sequences homologous to the *Glycine max* FAD2 and FATB genes, which is upstream of the nopaline right border sequence. The second T-DNA begins with the nopaline right border sequence, which is upstream of the antisense half of the inverted repeat containing sequences homologous to the *Glycine max* FAD2 and FATB genes, which is upstream of the 3' UTR of the *Gossypium barbadense* (Sea island cotton) H6 gene, which is upstream of the octopine left border sequence. The primer molecules derived from these sequences can be used as part of a primer set that also includes a DNA primer molecule derived from the genome flanking the transgene insert of event MON87705 as presented in SEQ ID NO: 3 and SEQ ID NO: 4.

The present invention includes a soybean plant comprising a DNA molecule comprising a polynucleotide having a sequence that is or is complementary to a sequence selected from the group consisting of SEQ ID NOs: 1, 2 and 18. In another aspect, the present invention includes a soybean plant part, where the plant part comprises a polynucleotide having a sequence that is or is complementary to a sequence selected from the group consisting of SEQ ID NOs: 1, 2 and 18. In another aspect, the present invention includes progeny of a soybean plant, where the progeny comprises a polynucleotide having a sequence that is or is complementary to a sequence selected from the group consisting of SEQ ID NOs: 1, 2 and 18.

The present invention also includes a soybean plant capable of producing seeds having an oil composition comprising approx. 55-80% oleic acid and less than 8% saturated fatty acid, wherein genetic determinants for said oil composition is obtainable from soybean having ATCC Accession No. PTA-9241. In another aspect, the present invention includes a method for producing a soybean plant comprising altered fatty acid levels, comprising crossing a plant comprising soybean event MON87705 with a soybean plant lacking soybean event MON87705 to obtain a plant comprising said soybean event MON87705 and altered fatty acid levels, wherein a representative sample of seed comprising said event was deposited under ATCC Accession No. PTA-9241. In a further aspect, the present invention also includes a method of producing a soybean variety comprising soybean event MON87705, comprising backcrossing soybean event MON87769 into said variety, wherein a representative sample of seed comprising said event was deposited under ATCC Accession No. PTA-9241.

The present invention also includes an oil composition obtained from seeds comprising a DNA molecule comprising a polynucleotide having a sequence that is or is complementary to a sequence selected from the group consisting of SEQ ID NOs: 1, 2 and 18. In another aspect, the present invention includes a commodity product derived from an oil composition selected from the group consisting of cooking oil, salad oil, shortening, lecithin, nontoxic plastics, printing inks, lubricants, waxes, hydraulic fluids, electric transformer fluids, solvents, cosmetics, hair care products and biodiesel.

The present invention also includes a DNA molecule comprising a polynucleotide having a sequence that is or is complementary to one selected from the group consisting of sequences listed under SEQ ID NOs: 1, 2 and 18. In antoher aspect, the present invention includes an isolated DNA molecule comprising at least from about 11 to about 20 consecutive nucleotides selected from the group consisting of SEQ ID NO: 1 and SEQ ID NO: 2.

The present invention also includes a genome of a soybean cell comprising a polynucleotide having a sequence selected from the group consisting of sequences listed under SEQ ID NOs: 1, 2 and 18.

In another aspect, the present invention includes a method of detecting the presence of soybean event MON87705 DNA in a biological sample comprising contacting the sample with a probe that hybridizes under stringent hybridization conditions with a sequence selected from the group consisting of SEQ ID NO: 1 and SEQ ID NO: 2, and their complements, and does not hybridize under stringent hybridization conditions with soybean plant genomic DNA that that does not comprise a sequence selected from the group consisting of SEQ ID NO: 1 and SEQ ID NO: 2, and their complements; subjecting the sample and probe to stringent hybridization conditions; and detecting binding of the probe to the sample; where binding is diagnostic for the presence of said DNA in the sample.

In another aspect, the present invention includes a method for detecting the presence of a nucleotide sequence diagnostic for the presence of soybean event MON87705 in a biological sample, comprising detecting the presence of a nucleotide sequence wherein said sequence is selected from the group consisting of SEQ ID NOs: 1, 2 and 18, wherein said biological sample is selected from the group consisting of soybean meal, soy flour, soy protein concentrate, soy protein isolates, texturized soy protein concentrate, hydrolyzed soy protein and whipped topping.

The present invention also includes a kit for detecting the presence or absence of soybean transgenic event MON87705 in a soybean sample comprising nucleotide components designed based on detecting one or more sequences shown under SEQ ID NOs: 1, 2 and 18. In another aspect, the present invention also includes a composition having a DNA molecule selected from the group consisting of SEQ ID NOs: 1, 2 and 18, wherein said composition is a commodity product selected from the group consisting of soybean meal, soy flour, soy protein concentrate, soy protein isolates, texturized soy protein concentrate, hydrolyzed soy protein and whipped topping.

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1

Transformation of Soybean A3525 with pMON95829 and Event Selection

The transgenic soybean plant MON87705 was generated by an *Agrobacterium*-mediated transformation of soybean cells with DNA fragments derived from pMON95829 (FIG. 1). The binary plant transformation vector, pMON95829 contains two plant transformation T-DNAs. Each T-DNA was flanked by right border (RB) and left border (LB) sequences at the ends of the T-DNAs. Post transformation screening of MON87705 identified a right border to right border co-integration of the two T-DNAs generating a two cassette insertion, one designed to express the aroA-CP4 gene from *Agrobacterium tumefaciens* imparting glyphosate tolerance and the other designed with an inverted repeat to trigger the RNAi based suppression of the endogenous FAD2 and FATB genes (SEQ ID NO: 7). The inverted repeat structure is not found in pMON95829, but is formed with a RB to RB co-integration of the two T-DNAs. This integration configuration yields a single transgenic locus containing both expression and suppression cassettes and is flanked by residual left border sequences (FIG. 2). The unique sequence generated at the RB:RB integration site is listed under SEQ ID NO: 18.

The T-DNAs are organized as follows: the first T-DNA begins with the octopine LB sequence, followed by the first artificial gene comprised of the 35S enhancer from figwort mosaic virus (FMV) and the promoter, intron, and leader sequence from the *Arabidopsis thaliana* Tsf1 gene, which is upstream of the ShkG transit peptide fused to an optimized aroA-CP4, which is upstream of the 3' UTR of the RbcS2 (E9) gene from *Pisum sativum*, followed by the second cassette which is comprised of the promoter and leader sequence from the *Glycine max* 7S alpha prime subunit of beta-conglycinin gene, which is upstream of the sense half of the inverted repeat containing sequences homologous to the *Glycine max* FAD2 and FATB genes, which is upstream of the nopaline RB sequence. The second T-DNA begins with the nopaline RB sequence, which is upstream of the antisense half of the inverted repeat containing sequences homologous to the *Glycine max* FAD2 and FATB genes, which is upstream of the 3' UTR of the *Gossypium barbadense* (Sea island cotton) H6 gene, which is upstream of the octopine LB sequence.

Explants transformed with pMON95829 were obtained via *Agrobacterium tumefaciens*-mediated transformation. Plants were regenerated from transformed tissue. Approximately 955 R0 transformation events were produced and were tested for the presence of the two T-DNAs by Invader® (Third Wave Technologies, Inc., Madison, Wis.). In addition, a PCR designed to identify the RB:RB configuration was used to select properly-assembled candidate events. R0 events demonstrating the proper co-integration of the T-DNAs were self-pollinated to generate R1 seed. The fatty acid composition of the R1 seed was determined by FAME-GC analysis. Based on these analyses, 48 events were carried forward to the R2 generation. Segregation of multi copy events and phenotypic characterization narrow the candidate event pool to 11 events by the R3 generation.

Detailed southern analysis designed to verify copy number, cassette intactness, locus and absence of undesired vector sequence was performed. In subsequent generations, field performance characteristics, as well as sequence flanking the insertion site for the remaining events, were also determined. One progeny line designated event MON87705 was selected based upon its overall fatty acid composition profile (Table 1), agronomic performance and molecular characteristics.

TABLE 1

Fatty Acid Composition Profile (weight % of total fatty acids)

| | Soy Line | | | | |
|---|---|---|---|---|---|
| | 16:0 | 18:0 | 18:1 | 18:2 | 18:3 |
| Wild type | 12.2 | 4.2 | 19.0 | 54.9 | 8.0 |
| MON87705 | 2.5 | 3.4 | 72.8 | 12.3 | 7.4 |

Example 2

Isolation of Flanking Sequences Using Inverse PCR

Sequences flanking the T-DNA insertion in MON87705 were determined using inverse PCR as described in Ochman et al., 1990 (PCR Protocols: A guide to Methods and Applications, Academic Press, Inc.) and by TAIL (Thermal Asymmetric InterLaced) PCR. Plant genomic DNA was isolated from both wild-type A3525 and the transgenic line from tissue grown under green house conditions. Frozen leaf tissue was ground by mortar and pestle with liquid nitrogen or mechanical grinding. A volume of 22 mL of extraction buffer was added to ~1 g of ground leaf tissue and incubated at 65° C. for 1 hour. The CTAB extraction buffer consisted of 1.4M NaCl, 2% CTAB, 20 mM EDTA, and 100 mM Tris-HCl pH 8.0. Just prior to use, 0.02% beta-mercaptoethanol and 0.5 mg RNase A was added to the extraction buffer. The samples were extracted with 12 mL of phenol/chloroform/isoamyl alcohol (25:24:1) solution and then centrifuged at 4000×G for 10 minutes at 4° C. The supernatant was transferred to a new tube and the DNA was precipitated with 15 mL of isopropanol. After centrifugation at 4000×G for 10 minutes, the pellets were washed with 5 mL 70% ethanol. A final centrifugation at 4000×G for 5 minutes was performed; the pellets were air dried and then re-suspended in 300 µL of water.

An aliquot of DNA was subjected to TAIL PCR and a region of sequence adjacent to the insertion site was isolated and sequenced. Additionally an aliquot of DNA was digested with restriction endonucleases selected based upon restriction analysis of the T-DNA. After self-ligation of restriction fragments, PCR was performed using primers designed from the T-DNA sequence that would amplify sequences extending away from the 5' and 3' ends of the T-DNA. PCR products were separated by agarose gel electrophoresis and purified using a QIAGEN gel purification kit (Qiagen, Valencia, Calif.). The subsequent products were sequenced directly using standard sequencing protocols.

Extension of the initial flanking sequence extending away from the 5' end of the T-DNA was performed using the Genomewalker™ kit (Clontech, Mountain View, Calif.). Standard protocol conditions were used and primers presented as SEQ ID NO: 19 and SEQ ID No: 20 were used in the nested PCR along with the supplied AP1 and AP2 primers. Reactions were run in duplicate and products were cloned and sequenced directly using standard sequencing protocols. Sequences were compared to the duplicate run, prior genomic sequences, and the 3' flanking sequence to determine actual polymorphisms from PCR-derived errors. There is apparently a chromosomal duplication that occurred upon generation of the MON87705 event. This region of duplication (SEQ ID NO: 17) corresponds to position 1053 through 3422 of SEQ ID NO: 6 and is nearly identical to position 10682 through 13051 of SEQ ID NO: 6. We have determined that there are two polymorphisms between the repeat located on the 5' end of the insert and the repeat from the 3' end of the insert, with the 3' end of the insert matching the original genomic sequence.

Using these methods, the identified 5' flanking sequence of the insertion was presented as SEQ ID NO: 3 (see FIG. 2), and the 3' flanking sequence was presented as SEQ ID NO: 4 (see FIG. 2). The portion of the inserted cassettes (SEQ ID NO: 7) from pMON95829 that was fully integrated into the A3525 genomic DNA is presented as SEQ ID NO: 5 (see FIG. 2).

Isolated sequences were compared to the T-DNA sequence to identify the flanking sequence and the co-isolated T-DNA fragment. Confirmation of the presence of the expression cassette was achieved by PCR with primers designed based upon the deduced flanking sequence data and the known T-DNA sequence. The A3525 wild type sequence corresponding to the same region in which the T-DNA was integrated in the transformed line was isolated using primers designed from the flanking sequences in MON87705. The flanking sequences in MON87705 and the A3525 wild type sequence were analyzed against multiple nucleotide and protein databases. This information was used to examine the relationship of the transgene to the plant genome and to look at the insertion site integrity. The flanking sequence and wild type sequences were used to design primers for TaqMan endpoint assays used to identify the events and determine zygosity as described in Example 3.

Example 3

Event-specific Endpoint TaqMan and Zygosity Assays

The methods used to identify event MON87705 in a sample are event-specific endpoint TaqMan PCR assays for which examples of conditions are described in Table 2 and Table 3. The first set of DNA primers that may be used in the endpoint assays are primers SQ20129 (SEQ ID NO: 8), SQ20130 (SEQ ID NO: 9) and 6FAM™ labeled primer PB10043 (SEQ ID NO: 10). The second set of DNA primers that may be used in the endpoint assays are primers SQ21928 (SEQ ID NO:11), SQ20901 (SEQ ID NO:12), and 6FAM™ labeled primer PB10164 (SEQ ID NO:13). 6FAM™ is a fluorescent dye product of Applied Biosystems (Foster City, Calif.) attached to the DNA primers. For TaqMan MGB (Minor Groove Binding) probes, the 5'exonuclease activity of Taq DNA polymerase cleaves the probe from the 5'-end, between the fluorophore and quencher. When hybridized to the target DNA strand, quencher and fluorophore are separated enough to produce a fluorescent signal.

SQ20129 (SEQ ID NO: 8) and SQ20130 (SEQ ID NO: 9) when used as described with PB10043 (SEQ ID NO: 10) produce a DNA amplicon that is diagnostic for event MON87705 DNA. SQ21928 (SEQ ID NO: 11) and SQ20901 (SEQ ID NO: 12) when used as described with PB10164 (SEQ ID NO: 13) produce a DNA amplicon that is also diagnostic for event MON87705 DNA. The controls for these analyses should include a positive control from soybean known to contain event MON87705 DNA, a negative control from non-transgenic soybean and a negative control that contains no template DNA. Similar assays can be designed for SEQ ID 18

These assays are optimized for use with an Applied Biosystems GeneAmp PCR System 9700, Stratagene Robocycler, MJ Engine, Perkin-Elmer 9700 or Eppendorf Mastercycler Gradient thermocycler. Other methods and apparatus may be known to those skilled in the art to produce amplicons that identify the event MON87705 DNA.

DNA amplification in a Stratagene Robocycler, MJ Engine, Perkin-Elmer 9700, Eppendorf Mastercycler Gradient thermocycler, Applied Biosystems GeneAmp PCR System 9700 or MJ Research DNA Engine PTC-225 thermal cycler is performed using the following cycling parameters. When running the PCR in the Eppendorf Mastercycler Gradient or MJ Engine, the thermocycler should be run in the calculated mode. When running the PCR in the Perkin-Elmer 9700, the thermocycler is run with the ramp speed set at maximum.

TABLE 2

Soybean MON87705 Event Specific Endpoint TaqMan PCR Assay

| Step | Reagent | Volume | Comments |
|---|---|---|---|
| 1 | 18 megohm water | adjust for final volume of 10 μl | |
| 2 | 2X Universal Master Mix | 5 μl | 1× final concentration of buffer |
| 3 | Event Primer-SQ20129 and SQ20130 Mix (or event primer SQ21928 and SQ20901) (resuspended in 18 megohm water to a concentration of 20 μM for each primer) Example: In a microcentrifuge tube, the following should be added to achieve 500 μl at a final concentration of 20 μM: 100 μl of Primer 1 at a concentration of 100 μM 100 μl of Primer 2 at a concentration of 100 μM 300 μl of 18 megohm water | 0.5 μl | 1.0 μM final concentration |
| 4 | Event 6-FAM ™ Probe PB10043 or PB10164 (resuspended in 18 megohm water to a concentration of 10 μM) Note: 6-FAM ™ Probe is light sensitive. | 0.2 μl | 0.2 μM final concentration |
| 5 | Internal Control Primer-SQ1532, SQ1533 Mix (resuspended in 18 megohm water to a concentration of 20 μM for each primer) | 0.5 μl | 1.0 μM final concentration |
| 6 | Internal Control VIC ™ Probe PB359 (resuspended in 18 megohm water to a concentration of 10 μM) Note: VIC ™ Probe is light sensitive. | 0.2 μl | 0.2 μM final concentration |
| 7 | Extracted DNA (template): Leaf Samples to be analyzed | 3.0 μl | |

TABLE 2-continued

Soybean MON87705 Event Specific Endpoint TaqMan PCR Assay

| Step | Reagent | Volume | Comments |
|---|---|---|---|
| | Negative control (non-transgenic DNA) Negative water control (No template control) Positive control GM_A94978 DNA | | |

TABLE 3

Endpoint TaqMan thermocycler conditions

| Cycle No. | Settings |
|---|---|
| 1 | 50° C. 2 minutes |
| 1 | 95° C. 10 minutes |
| 10 | 95° C. 15 seconds |
| | 64° C. 1 minute |
| | −1° C./cycle |
| 30 | 95° C. 15 seconds |
| | 54° C. 1 minute |
| 1 | 10° C. Forever |

Determining zygosity for event MON87705 in a sample was done using an event-specific zygosity endpoint TaqMan PCR assay for which examples of conditions are described in Table 4 and Table 5. The DNA primers used in the zygosity assay are primers SQ20901 (SEQ ID NO: 12), SQ21928 (SEQ ID NO: 11), SQ21905 (SEQ ID NO: 15), 6FAM™ labeled primer PB10164 (SEQ ID NO: 13) and VIC™ labeled primer PB10335 (SEQ ID NO: 14). 6FAM™ and VIC™ are fluorescent dye products of Applied Biosystems (Foster City, Calif.) attached to the DNA primers.

SQ20901 (SEQ ID NO: 12) and SQ21928 (SEQ ID NO: 11) when used in these reaction methods with PB10164 (SEQ ID NO: 13) produce a DNA amplicon that is diagnostic for event MON87705 DNA. The controls for this analysis should include a positive control from soybean containing event MON87705 DNA, a negative control from non-transgenic soybean and a negative control that contains no template DNA. SQ21928 (SEQ ID NO: 11) and SQ21905 (SEQ ID NO: 15) when used in these reaction methods with PB10335 (SEQ ID NO: 14) produce a DNA amplicon that is diagnostic for the wild type allele and contains SEQ ID NO: 16 in its entirety. Heterozygosity is determined by the presence of both amplicons demonstrated by the liberation of fluorescent signal from both probes PB10164 and PB10335.

These assays are optimized for use with an Applied Biosystems GeneAmp PCR System 9700, Stratagene Robocycler, MJ Engine, Perkin-Elmer 9700 or Eppendorf Mastercycler Gradient thermocycler. Other methods and apparatus known to those skilled in the art that produce amplicons that identify the event MON87705 DNA is within the skill of the art.

DNA amplification in a Stratagene Robocycler, MJ Engine, Perkin-Elmer 9700, Eppendorf Mastercycler Gradient thermocycler, Applied Biosystems GeneAmp PCR System 9700 or MJ Research DNA Engine PTC-225 thermal cycler is performed using the following cycling parameters. When running the PCR in the Eppendorf Mastercycler Gradient or MJ Engine, the thermocycler should be run in the calculated mode. When running the PCR in the Perkin-Elmer 9700, the thermocycler is run with the ramp speed set at maximum.

TABLE 4

Soybean MON87705 Event-Specific Zygosity Endpoint TaqMan PCR

| Step | Reagent | Volume | Comments |
|---|---|---|---|
| 1 | 18 megohm water | adjust for final volume of 10 μl | |
| 2 | 2X Universal Master Mix | 5 μl | 1X final concentration |
| 3 | Zygosity primer - SQ20901, SQ21928, SQ21905 (resuspended in 18 megohm water to a concentration of 20 μM for each primer) Example: In a microcentrifuge tube, the following should be added to achieve 500 μl at a final concentration of 20 μM: 100 μl of each primer at a concentration of 100 μM 200 μl of 18 megohm water | 0.5 μl | 1 μM final concentration |
| 4 | Event 6-FAM ™ Probe (PB10164) (resuspended in 18 megohm water to a concentration of 10 μM) Note: 6-FAM ™ Probe is light sensitive. | 0.2 μl | 0.20 μM final concentration |
| 5 | Wild Type VIC ™ Probe (PB10335) (resuspended in 18 megohm water to a concentration of 10 μM) Note: VIC ™ Probe is light sensitive. | 0.2 μl | 0.20 μM final concentration |
| 6 | Extracted DNA (template): Leaf Samples to be analyzed Negative control (non-transgenic DNA) | 3.0 μl | |

TABLE 4-continued

Soybean MON87705 Event-Specific Zygosity Endpoint TaqMan PCR

| Step | Reagent | Volume | Comments |
|---|---|---|---|
| | Negative water control (No template control) | | |
| | Positive control Homozygous GM_A94978 DNA | | |
| | Positive control Hemizygous GM_A94978 DNA | | |

TABLE 5

Zygosity Endpoint TaqMan thermocycler conditions

| Cycle No. | Settings |
|---|---|
| 1 | 50° C. 2 minutes |
| 1 | 95° C. 10 minutes |
| 10 | 95° C. 15 seconds |
| | 64° C. 1 minute |
| | −1° C./cycle |
| 30 | 95° C. 15 seconds |
| | 54° C. 1 minute |
| 1 | 10° C. Forever |

Example 4

Identification of Event MON87705 in a Given Soybean Sample

The following example describes how one may identify the presence or absence of MON87705 event in a given soybean sample.

DNA event primer pairs are used to produce an amplicon diagnostic for soybean event MON87705. An amplicon diagnostic for MON87705 comprises at least one junction sequence: SEQ ID NO: 1, SEQ ID NO: 2 or SEQ ID NO: 18. SEQ ID NO: 1 (FIG. 2) is a nucleotide sequence corresponding to the junction of the 5' flanking sequence (positions 3413 through 3422 of SEQ ID NO: 6, see FIG. 2) and the integrated border of the insertion (positions 3423 through 3433 of SEQ ID NO: 6, see FIG. 2). SEQ ID NO: 2 (see FIG. 2) is a nucleotide sequence corresponding to the junction of the integrated border of the insertion (positions 10664 through 10673 of SEQ ID NO: 6, see FIG. 2) and the 3' flanking sequence (positions 10674 through 10683 of SEQ ID NO: 6, see FIG. 2). SEQ ID NO: 18 is a nucleotide sequence corresponding to the right border to right border junction (positions 9230 to 9335 of SEQ ID NO: 6) generated upon the cointegration of the two pMON95829 T-DNAs to yield event MON87705

Event primer pairs that will produce a diagnostic amplicon for MON87705 include primer pairs based upon the flanking sequences and the inserted cassettes. To acquire a diagnostic amplicon in which at least 11 nucleotides of SEQ ID NO: 1 is found, one would design a forward primer based upon SEQ ID NO: 3 from bases 1 through 3448 and a reverse primer based upon the inserted cassette, SEQ ID NO: 5 from positions 10 through 7251. To acquire a diagnostic amplicon in which at least 11 nucleotides of SEQ ID NO: 2 is found, one would design a forward primer based upon the inserted cassette, SEQ ID NO: 5, from positions 1 through 7241 and a reverse primer based upon the 3' flanking sequence, SEQ ID NO: 4, from bases 10 through 2515. For practical purposes, one should design primers which produce amplicons of a limited size range, preferably between 200 to 1000 bases. Smaller sized amplicons in general are more reliably produced in PCR reactions, allow for shorter cycle times and can be easily separated and visualized on agarose gels or adapted for use in endpoint TaqMan-like assays. In addition, amplicons produced using said primer pairs can be cloned into vectors, propagated, isolated and sequenced or can be sequenced directly with methods well established in the art. Any primer pair derived from the combination of SEQ ID NO: 3 and SEQ ID NO: 5 or the combination of SEQ ID NO: 4 and SEQ ID NO: 5 that are useful in a DNA amplification method to produce an amplicon diagnostic for MON87705 or progeny thereof is an aspect of the present invention. Any single isolated DNA polynucleotide primer molecule comprising at least 11 contiguous nucleotides of SEQ ID NO: 3, or its complement that is useful in a DNA amplification method to produce an amplicon diagnostic for MON87705 or progeny thereof is an aspect of the present invention. Any single isolated DNA polynucleotide primer molecule comprising at least 11 contiguous nucleotides of SEQ ID NO: 4, or its complement that is useful in a DNA amplification method to produce an amplicon diagnostic for MON87705 or progeny thereof is an aspect of the present invention. Any single isolated DNA polynucleotide primer molecule comprising at least 11 contiguous nucleotides of SEQ ID NO: 5, or its complement that is useful in a DNA amplification method to produce an amplicon diagnostic for MON87705 or progeny thereof is an aspect of the present invention.

An example of the amplification conditions for this analysis is illustrated in Table 6 and Table 7. However, any modification of these methods or the use of DNA primers homologous or complementary to SEQ ID NO: 3 or SEQ ID NO: 4 or DNA sequences of the genetic elements contained in the transgene insert (SEQ ID NO: 5) of MON87705 that produce an amplicon diagnostic for MON87705, is within the art. A diagnostic amplicon comprises a DNA molecule homologous or complementary to at least one transgene/genomic junction DNA listed under SEQ ID NO: 1, 2 and 18, or a substantial portion thereof.

An analysis for event MON87705 plant tissue sample should include a positive tissue control from event MON87705, a negative control from a soybean plant that is not event MON87705, for example, but not limited to A3525, and a negative control that contains no soybean genomic DNA. A primer pair that will amplify an endogenous soybean DNA molecule will serve as an internal control for the DNA amplification conditions. Additional primer sequences can be selected from SEQ ID NO: 3, SEQ ID NO: 4, or SEQ ID NO: 5 by those skilled in the art of DNA amplification methods, and conditions selected for the production of an amplicon by the methods shown in Table 6 and Table 7 may differ, but result in an amplicon diagnostic for event MON87705 DNA. The use of these DNA primer sequences with modifications to the methods of Table 6 and Table 7 are within the scope of the invention. The amplicon produced by at least one DNA primer sequence derived from SEQ ID NO: 3, SEQ ID NO: 4 or SEQ ID NO: 5 that is diagnostic for MON87705 is an aspect of the invention.

DNA detection kits that contain at least one DNA primer derived from SEQ ID NO: 3, SEQ ID NO: 4 or SEQ ID NO: 5, that when used in a DNA amplification method, produces a diagnostic amplicon for MON87705 or its progeny is an aspect of the invention. A soybean plant or seed, wherein its genome will produce an amplicon diagnostic for MON87705 when tested in a DNA amplification method is an aspect of the invention. The assay for the MON87705 amplicon can be performed by using an Applied Biosystems GeneAmp PCR System 9700, Stratagene Robocycler, MJ Engine, Perkin-Elmer 9700 or Eppendorf Mastercycler Gradient thermocycler or any other amplification system that can be used to produce an amplicon diagnostic of MON87705 as shown in Table 7.

TABLE 6

Soybean MON87705 Event Specific PCR Assay

| Step | Reagent | Volume | Comments |
|---|---|---|---|
| 1 | 18 megohm water | adjust for final volume of 10 ul | |
| 2 | 2× Universal Master Mix (Contains dNTPs, enzyme and buffer) | 5.0 ul | 1× final concentration of dNTPs, enzyme and buffer |
| 3 | Primer-1 and Primer-2 Mix (resuspended in 18 megohm water to a concentration of 20 uM for each primer) Example: In a microcentrifuge tube, the following should be added to achieve 500 ul at a final concentration of 20uM: 100 ul of Primer 1 at a concentration of 100 uM 100 ul of Primer 2 at a concentration of 100 uM 300 ul of 18 megohm water | 0.5 ul | 1.0 uM final concentration |
| 5 | Extracted DNA (template) 50 ng of genomic DNA: Leaf samples to be analyzed Negative control (non-transgenic DNA) Negative water control (no template control) Positive control MON88769 DNA | 3.0 ul | |

TABLE 7

Soybean MON87705 Event Thermocycler Conditions

| Cycle No. | Settings |
|---|---|
| 1 | 50° C. 2 minutes |
| 1 | 95° C. 10 minutes |
| 10 | 95° C. 15 seconds |
| | 64° C. 1 minute |
| | −1° C./cycle |
| 30 | 95° C. 15 seconds |
| | 54° C. 1 minute |
| 1 | 10° C. Forever |

A deposit of seeds of the soybean event MON87705 disclosed above and recited in the claims, has been made under the Budapest Treaty with the American Type Culture Collection (ATCC), 10801 University Boulevard, Manassas, Va. 20110. The ATCC accession number is PTA-9241. The deposit will be maintained in the depository for a period of 30 years, or 5 years after the last request, or for the effective life of the patent, whichever is longer, and will be replaced as necessary during that period.

Having illustrated and described the principles of the present invention, it should be apparent to persons skilled in the art that the invention can be modified in arrangement and detail without departing from such principles. We claim all modifications that are within the spirit and scope of the appended claims.

We claim:

1. A method of detecting the presence of soybean event MON87705 DNA in a biological sample comprising:
   i. contacting the sample with a probe that hybridizes under stringent hybridization conditions with a sequence selected from the group consisting of SEQ ID NO: 1, SEQ ID NO: 2, SEQ ID NO: 18, and their complements, and does not hybridize under stringent hybridization conditions with soybean plant genomic DNA that that does not comprise a sequence selected from the group consisting of SEQ ID NO: 1 SEQ ID NO: 2, SEQ ID NO: 18, and their complements;
   ii. subjecting the sample and probe to stringent hybridization conditions; and
   iii. detecting binding of the probe to said sample;
wherein binding is diagnostic for the presence of said DNA in said sample.

2. The method of claim 1, wherein said probe comprises SEQ ID NO: 1 and is a Polymerase Chain Reaction (PCR) amplicon produced using a DNA primer pair comprising at least 15 consecutive nucleotides each of SEQ ID NO: 3 and SEQ ID NO: 5, or their complements.

3. The method of claim 1, wherein said probe comprises SEQ ID NO: 2 and is a Polymerase Chain Reaction (PCR) amplicon produced using a DNA primer pair comprising at least 15 consecutive nucleotides each of SEQ ID NO: 5 and SEQ ID NO: 4, or their complements.

4. The method of claim 1, wherein said probe comprises SEQ ID NO: 18 and is a Polymerase Chain Reaction (PCR) amplicon produced using a DNA primer pair comprising a first primer of at least 15 consecutive nucleotides of SEQ ID NO: 5 from position 1 to position 5705, or a complement thereof, and a second primer of SEQ ID NO: 5 from position 5914 to 7251, or a complement thereof, and said PCR amplicon comprises SEQ ID NO: 18.

5. A method for detecting the presence of a nucleotide sequence diagnostic for the presence of soybean event MON87705 in a biological sample, comprising obtaining a biological sample having nucleic acids, and detecting the presence of a nucleotide sequence wherein said sequence is selected from the group consisting of SEQ ID NOs: 1, 2 and 18.

6. The method of claim 5, wherein said biological sample is selected from the group consisting of soybean meal, soy flour, soy protein concentrate, soy protein isolates, texturized soy protein concentrate, hydrolyzed soy protein and whipped topping.

7. The method of claim 5, further comprising:
  i. obtaining a template DNA from said biological sample;
  ii. contacting said template DNA with a first and second DNA primer of at least 15 consecutive nucleotides of SEQ ID NO: 6;
  iii. performing a nucleic acid amplification on said template DNA to prepare an amplicon wherein said amplicon comprises a nucleic acid sequence selected from the group consisting of SEQ ID NOs: 1, 2, 18, and their complements, and
  iv. detecting said amplicon.

8. The method of claim 7, wherein said nucleic acid amplification is a Polymerase Chain Reaction (PCR).

9. The method of claim 7, wherein said first and said second primers of SEQ ID NO: 6 comprise at least 15 consecutive nucleotides each of SEQ ID NO: 3 and SEQ ID NO: 5, or their complements.

10. The method of claim 7, wherein said first and said second primers of SEQ ID NO: 6 comprise at least 15 consecutive nucleotides each of SEQ ID NO: 5 and SEQ ID NO: 4, or their complements.

11. The method of claim 7, wherein said first and said second primers of SEQ ID NO: 6 comprise a first primer of SEQ ID NO: 5 from position 1 to position 5705, or a complement thereof, and a second primer of SEQ ID NO: 5 from position 5914 to 7251, or a complement thereof, and said amplicon comprises SEQ ID NO: 18.

12. The method of claim 7, wherein at least one DNA primer of said first and said second primers of SEQ ID NO: 6 is selected from the group consisting of SEQ ID NOs: 8 to 16.

13. The method of claim 7, wherein at least one primer of said first and said second primers of SEQ ID NO: 6 is at least 18 nucleotides long or at least 20 nucleotides long.

14. The method of claim 7, wherein said first and said second primers of SEQ ID NO: 6 are at least 18 nucleotides long.

* * * * *

SEQUENCE LISTING

<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: 5' Junction sequence

<400> SEQUENCE: 1
aagtttgtgg ttcatgtccg                                                 20

<210> SEQ ID NO 2
<211> LENGTH: 20
<212> TYPE: DNA
<213> ORGANISM: Artificial Sequence
<220> FEATURE:
<223> OTHER INFORMATION: 3' Junction Sequence

<400> SEQUENCE: 2
tacaattgaa gagactcagg                                                 20

<210> SEQ ID NO 3
<211> LENGTH: 3458
<212> TYPE: DNA
<213> ORGANISM: Glycine max
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (125)..(125)
<223> OTHER INFORMATION: n is a, c, g, or t
<220> FEATURE:
<221> NAME/KEY: misc_feature
<222> LOCATION: (729)..(729)
<223> OTHER INFORMATION: n is a, c, g, or t
<220> FEATURE:
<221> NAME/KEY: misc_feature
<222> LOCATION: (855)..(855)
<223> OTHER INFORMATION: n is a, c, g, or t
<220> FEATURE:
<221> NAME/KEY: misc_feature
<222> LOCATION: (1203)..(1203)
<223> OTHER INFORMATION: n is a, c, g, or t
<220> FEATURE:
<221> NAME/KEY: misc_feature
<222> LOCATION: (1243)..(1243)
<223> OTHER INFORMATION: n is a, c, g, or t
<220> FEATURE:
<221> NAME/KEY: misc_feature
<222> LOCATION: (1522)..(1522)
<223> OTHER INFORMATION: n is a, c, g, or t

<400> SEQUENCE: 3
actatagggc acgcgtggtc gacggnccgg gctggtaaac ttaacaaagc cttatatgga     60
cttaaacaag cttccaaagc ttggtatgga aaactaagtt catttatttt ggaaaatggc    120
tttgnacatg gaatggtcga cacaacactc tttcctaaga attatgattc tcaattttta    180
ttagtacaag tgtatgtgga tgatatcatt tttggtgcta ctaatgaaat gctctatgaa    240
gatttttcta agttaatgca aactgagttt gaaatgagca tgatgggaga gctaaaattc    300
ttccttggac tgcaaataaa gcaaacaccc caaggcattt acattcatca gaccaagtat    360
gtgaaaaatt agttgaagaa gttcaacata agtgatgaaa agagatgaa gactttatg      420 catcccacta cacatcttgg actggatgag gaatcaatga aggtggacgt gactcaatac    480
aaagcaatga ttggatcact gctctatctt aatgcttcta ggccttatat aattttagt     540

```
gttttattat gtgcaagatt ccaaaaggaa ccaagggaag ttcatttaac tgcagttaaa      600
cctatattct aatatttaat tagaactcat aaccttggtc ttatgcttaa gagaagagat      660
agtttcagac tcatgagcta ttgagatgtg gactatgttg gtgataaagt cgaaagaaaa      720
agtacaagng gaagttgtca ctttataggt ggcaacttag tcacttggat atggaagaag      780
tagggatcaa ctacattgtt cactgctgaa gtagaatgcg tgtcagtagc catggaggtt      840
accctcgaca ttgangaccc caagaaatag gttcaaagtt ttggaaatcc acagggtcag      900
agcacaagtg caagtttcaa gtatcaaggc agcaacgaag ctatatcgta ggtaggggag      960
tttagtggta ccaataatgc ccaaacaccc actggtggga ctcaaaatct acaagggag     1020 agcagaatgt cttctacatc atcaatatcc aaaccaagat tctcaagacc gtgaaacaaa     1080
ggatctcagg gtgttgttat cactgcggtt tggccttggg gccaaggcac tgttgtcctg     1140
aaaaaaatat gagagttgta atactcgcta aggatgagta gattaatgaa gacggggaga     1200
tcntaggatt aaaaaatgag aatgaggaag aatgtgagga agntttggag atggtttgct     1260
agcggatgga tttgtcagtt tgttccgcag gtgggctaac ccagcctcaa gcatgaagct     1320
taggtgagaa ttatagggc aagaggtgat aatcttgatt gacaataggg caagccacaa     1380
ctttatatcc aacaaattgg tacataaatt gggactcagc atagatccca caaagcccta     1440
ttatatgaga ttgggggata gtaaccgcaa atccactcaa ggatgttgta agaacttaaa     1500
aaatagttgg gagcttatac cntggtagga tatttctatc tatttaagtt gggaggagtg     1560
gacctaatta ttggagttgc ttagttgaa acattgggag aaattaaggt gaattggagg     1620
accctaagta tgtcttttgt ccaccaagat cagaatatgg tgatcaagga gatcttggtt     1680
tattgaagac aatgatcatt tgagaacat tgcaaaaaat agttagcaag gaagttgaga     1740
tgatgttcat gttgtgggta attgaaagca actatgtgga acaaattgat ttaacaaaga     1800
accaagaaaa ttagttgtag caagtactga tagagttttgc tacagttttt caggacctaa     1860
gggtttacca ccatctagag aggttgatca caagattgca attaagtccg ggcatatcc     1920 agataatgtt aggccttatc gttaccccca cttacagaag aatgagataa aaactctagt     1980
ggttgagatg ttatgattgg ggattattag actaagcaat agctcctatt ctagcccagt     2040
aattttggta aaaggaaag atggaagttg acgattatgt atggattatc aggctttaag     2100
taaggctaca gtcccagaca agttcctgat tcctgtcatg aaagagttgt tggatgagtt     2160
aaatggaccc atccacttct ctaaaataga tctaaaggca aggtatcacc aaatcagaat     2220
gcacaaacct accttcagaa ctcaccaagg acattatgaa tctccagtga tgccatttgg     2280
attaacaaac accccgacca cgttccaatg agctatgaat gccacactga aaccgttcct     2340
tcgtaggtat gtggtagtgt tctttgatga cattttggtc tatagtaagt cttgggaagc     2400
ccatttggat catttgagtt aggtgttggc caggttatta gaacattatt tcttcacaaa     2460 tgttttaaa aaaaaatgta gttttggtca aattaaggcg ggttgcttag gcacgttat     2520 ctctaaagaa ggagttttga tgaggccatt ttgtagtggc caatgcctaa aactcctaag     2580
tctttgagag ggttttttgga acttacaggt tattataaaa ggtccatttg caattatggg     2640
aagatagctc gcccattgat tgatctatta agtaaggaa attttaagtg gaatgaggat     2700
agtattaagg cttccataca attacaacaa gctattacca caataccaac actatccatg     2760
cttgattttt caaacacaatt ctccatagaa tgtgatgcct cggggaaggg aattggagtt     2820
gttctaacac aagatagaaa gcaaattgct tatttcaaca aggcattaaa agatttgact     2880
```

-continued

| | |
|---|---|
| ctttctaaat ctatgtatga aaaggaatca atggctcttg tcttagccat acaacattgg | 2940 |
| aggcettate ttccggatta gaaatttact atatacattg accaaaaaag tttgagatat | 3000 |
| ctactagatc agcgaattac aactcaacca acaatattgg gtagccaagt tgctggggta | 3060 |
| tgagtttgac attgtgtata aggtgggggc ttcaaacaag gttgttgatg ctctatctag | 3120 |
| aagagatgaa gacaaagaat tgcagggcat ttctagacct ttctggaaag acataacaaa | 3180 |
| aattaatgaa gaagttcaga aggatcccgc gttggctaaa atccgagaag aattgaagga | 3240 |
| taatctagat tcacaccctc agtacaccct ggagtgtgac atattatact tcagagggag | 3300 |
| gttggtccta ttagcttctt cattgtggat tccaaagtta ctacaagaat tccagacttc | 3360 |
| tcttatggga gggcactcgg gtatttacat aacttataga agaatcactc aatcgcttta | 3420 |
| ttggatacca ataaagggag aaatcactaa gtttgtgg | 3458 |

<210> SEQ ID NO 4
<211> LENGTH: 2515
<212> TYPE: DNA
<213> ORGANISM: Glycine max

<400> SEQUENCE: 4

| | |
|---|---|
| gagactcagg gtgttgttat cactgcggtt tggcctttgg gccaaggcac cgttgtcctg | 60 |
| aaaaaaatat gagagttgta atactcgcta aggatgagta gattaatgaa gacggggaga | 120 |
| tcataggatt aaaaaatgag aatgaggaag aatgtgagga agttttggag atggtttgct | 180 |
| agcggatgga tttgtcagtt tgttccgcag gtgggctaac ccagcctcaa gcatgaagct | 240 |
| taggtgagaa ttataggggc aagaggtgat aatcttgatt gacaataggg caagccacaa | 300 |
| ctttatatcc aacaaattgg tacataaatt gggactcagc atagatccca caaagcccta | 360 |
| ttatatgaga ttgggggata gtaaccgcaa atccactcaa ggatgttgta agaacttaaa | 420 |
| aaatagttgg gagcttatac catggtagga tatttctatc tatttaagtt gggaggagtg | 480 |
| gacctaatta ttggagttgc ttagttggaa acattgggag aaattaaggt gaattggagg | 540 |
| accctaagta tgtcttttgt ccaccaagat cagaatatgg tgatcaagga gatcttggtt | 600 |
| tattgaagac aatgatcatt tgagaacat tgcaaaaaat agttagcaag gaagttgaga | 660 |
| tgatgttcat gttgtgggta attgaaagca actatgtgga acaaattgat ttaacaaaga | 720 |
| accaagaaaa ttagttgtag caagtactga tagagtttgc tacagttttt caggacctaa | 780 |
| gggtttacca ccatctagag aggttgatca caagattgca attaagtccg ggcatatcc | 840 |
| agataatgtt aggccttatc gttaccccca cttacagaag aatgagataa aaactctagt | 900 |
| ggttgagatg ttatgattgg ggattattag actaagcaat agctcctatt ctagcccagt | 960 |
| aattttggta aaaggaaag atggaagttg acgattatgt atggattatc aggctttaag | 1020 |
| taaggctaca gtcccagaca gttcctgat tcctgtcatg aaagagttgt tggatgagtt | 1080 |
| aaatggaccc atccacttct ctaaaataga tctaaaggca aggtatcacc aaatcagaat | 1140 |
| gcacaaacct accttcagaa ctcaccaagg acattatgaa tctccagtga tgccatttgg | 1200 |
| attaacaaac accccgacca cgttccaatg agctatgaat gccacactga accgttcct | 1260 |
| tcgtaggtat gtggtagtgt tctttgatga cattttggtc tatagtaagt cttgggaagc | 1320 |
| ccatttggat catttgagtt aggtgttggc caggttatta gaacattatt tcttcacaaa | 1380 |
| tgttttaaa aaaaaatgta gttttggtca aattaaggcg ggttgcttag gcacgttat | 1440 |
| ctctaaagaa ggagttttga tgaggccatt ttgtagtggc caatgcctaa aactcctaag | 1500 |
| actttgagag ggttttggaa acttacaggt tattataaaa ggtccatttg caattatggg | 1560 |

| | |
|---|---:|
| aagatagctc gcccattgat tgatctatta aagtaaggaa attttaagtg gaatgaggat | 1620 |
| agtattaagg cttccataca attacaacaa gctattacca caataccaac actatccatg | 1680 |
| cttgattttt caaaacaatt ctccatagaa tgtgatgcct cggggaaggg aattggagtt | 1740 |
| gttctaacac aagatagaaa gcaaattgct tatttcaaca aggcattaaa agatttgact | 1800 |
| cttttctaaat ctatgtatga aaaggaatca atggctcttg tcttagccat acaacattgg | 1860 |
| aggccttatc ttccggatta gaaatttact atatacattg accaaaaaag tttgagatat | 1920 |
| ctactagatc agcgaattac aactcaacca acaatattgg gtagccaagt tgctggggta | 1980 |
| tgagtttgac attgtgtata aggtgggggc ttcaaacaag gttgttgatg ctctatctag | 2040 |
| aagagatgaa gacaaagaat tgcagggcat ttctagacct ttctggaaag acataacaaa | 2100 |
| aattaatgaa gaagttcaga aggatcccgc gttggctaaa atccgagaag aattgaagga | 2160 |
| taatctagat tcacaccctc agtacaccct ggagtgtgac atattatact tcagagggag | 2220 |
| gttggtccta ttagcttctt cattgtggat tccaaagtta ctacaagaat tccagacttc | 2280 |
| tcttatggga gggcactcgg gtatttacat aacttataga agaatcactc aatcgcttta | 2340 |
| ttggatacca ataaagggag aaatcactaa gtttgtggtt gcgtgtcatg tgggccaaag | 2400 |
| aagtaaatat caagcatcct ctccagcagg tttactacaa cctttgccaa ttccaaatgc | 2460 |
| tatttgggaa gaaattagta tgaattttat tgtaggtatg ctaaaatcaa aaggg | 2515 |

<210> SEQ ID NO 5
<211> LENGTH: 7251
<212> TYPE: DNA
<213> ORGANISM: Artificial Sequence
<220> FEATURE:
<223> OTHER INFORMATION: Inserted cassettes

<400> SEQUENCE: 5

| | |
|---|---:|
| ttcatgtccg ggaaatctac atggatcagc aatgagtatg atggtcaata tggagaaaaa | 60 |
| gaaagagtaa ttaccaattt tttttcaatt caaaaatgta gatgtccgca gcgttattat | 120 |
| aaaatgaaag tacattttga taaaacgaca aattacgatc cgtcgtattt ataggcgaaa | 180 |
| gcaataaaca aattattcta attcggaaat ctttatttcg acgtgtctac attcacgtcc | 240 |
| aaatgggggc ttagatgaga aacttcacga tcgatgcggc cgtcgagtgg aagctaattc | 300 |
| tcagtccaaa gcctcaacaa ggtcaggta cagagtctcc aaaccattag ccaaaagcta | 360 |
| caggagatca atgaagaatc ttcaatcaaa gtaaactact gttccagcac atgcatcatg | 420 |
| gtcagtaagt ttcagaaaaa gacatccacc gaagacttaa agttagtggg catctttgaa | 480 |
| agtaatcttg tcaacatcga gcagctggct tgtggggacc agacaaaaaa ggaatggtgc | 540 |
| agaattgtta ggcgcaccta ccaaaagcat ctttgccttt attgcaaaga taaagcagat | 600 |
| tcctctagta caagtgggga acaaaataac gtggaaaaga gctgtcctga cagcccactc | 660 |
| actaatgcgt atgacgaacg cagtgacgac cacaaaagaa ttagcttgag ctcaggattt | 720 |
| agcagcattc cagattgggt tcaatcaaca aggtacgagc catatcactt tattcaaatt | 780 |
| ggtatcgcca aaaccaagaa ggaactccca tcctcaaagg tttgtaagga agaattcgat | 840 |
| atcaagcttg atatcggaag tttctctctt gagggaggtt gctcgtggaa tgggacacat | 900 |
| atggttgtta ataaaaccca tttccattgt catgagattt tgaggttaat atatactta | 960 |
| cttgttcatt atttatttg gtgtttgaat aaatgatata aatggctctt gataatctgc | 1020 |
| attcattgag atatcaaata tttactctag agaagagtgt catatagatt gatggtccac | 1080 |

```
aatcaatgaa attttggga gacgaacatg tataaccatt tgcttgaata accttaatta      1140
aaaggtgtga ttaaatgatg tttgtaacat gtagtactaa acattcataa aacacaacca      1200
acccaagagg tattgagtat tcacggctaa acagggcat aatggtaatt taaagaatga       1260
tattatttta tgttaaaccc taacattggt ttcggattca acgctataaa taaaaccact      1320
ctcgttgctg attccattta tcgttcttat tgaccctagc cgctacacac ttttctgcga      1380
tatctctgag gtaagcgtta acgtaccctt agatcgttct ttttcttttt cgtctgctga      1440
tcgttgctca tattatttcg atgattgttg gattcgatgc tctttgttga ttgatcgttc      1500
tgaaaattct gatctgttgt ttagatttta tcgattgtta atatcaacgt ttcactgctt      1560
ctaaacgata atttattcat gaaactattt tcccattctg atcgatcttg ttttgagatt      1620
ttaatttgtt cgattgattg ttggttggtg gatctatata cgagtgaact tgttgatttg      1680
cgtatttaag atgtatgtcg atttgaattg tgattgggta attctggagt agcataacaa      1740
atccagtgtt ccctttttct aagggtaatt ctcggattgt ttgctttata tctcttgaaa      1800
ttgccgattt gattgaattt agctcgctta gctcagatga tagagcacca caattttgt       1860 ggtagaaatc ggtttgactc cgatagcggc ttttactat gattgtttg tgttaaagat        1920 gattttcata atgttatat atgtctactg ttttattga ttcaatattt gattgttctt        1980 tttttgcag atttgttgac cagagatcta ccatggcgca agttagcaga atctgcaatg       2040
gtgtgcagaa cccatctctt atctccaatc tctcgaaatc cagtcaacgc aaatctccct      2100
tatcggtttc tctgaagacg cagcagcatc cacgagctta tccgatttcg tcgtcgtggg      2160
gattgaagaa gagtgggatg acgttaattg gctctgagct tcgtcctctt aaggtcatgt      2220
cttctgtttc cacggcgtgc atgcttcacg gtgcaagcag ccgtccagca actgctcgta      2280
agtcctctgg tctttctgga accgtccgta ttccaggtga caagtctatc tcccacaggt      2340
ccttcatgtt tggaggtctc gctagcggtg aaactcgtat caccggtctt ttggaaggtg      2400
aagatgttat caacactggt aaggctatgc aagctatggg tgccagaatc cgtaaggaag      2460
gtgatacttg gatcattgat ggtgttggta acggtggact ccttgctcct gaggctcctc      2520
tcgatttcgg taacgctgca actggttgcc gtttgactat gggtcttgtt ggtgtttacg      2580
atttcgatag cactttcatt ggtgacgctt ctctcactaa gcgtccaatg ggtcgtgtgt      2640
tgaacccact tcgcgaaatg ggtgtgcagg tgaagtctga agacggtgat cgtcttccag      2700
ttaccttgcg tggaccaaag actccaacgc caatcaccta cagggtacct atggcttccg      2760
ctcaagtgaa gtccgctgtt ctgcttgctg gtctcaacac cccaggtatc accactgtta      2820
tcgagccaat catgactcgt gaccacactg aaaagatgct tcaaggtttt ggtgctaacc      2880
ttaccgttga gactgatgct gacggtgtgc gtaccatccg tcttgaaggt cgtggtaagc      2940
tcaccggtca agtgattgat gttccaggtg atccatcctc tactgctttc ccattggttg      3000
ctgccttgct tgttccaggt tccgacgtca ccatccttaa cgttttgatg aacccaaccc      3060
gtactggtct catcttgact ctgcaggaaa tgggtgccga catcgaagtg atcaacccac      3120
gtcttgctgg tggagaagac gtggctgact gcgtgttcg ttcttctact ttgaagggtg       3180
ttactgttcc agaagaccgt gctccttcta tgatcgacga gtatccaatt ctcgctgttg      3240
cagctgcatt cgctgaaggt gctaccgtta tgaacggttt ggaagaactc cgtgttaagg      3300
aaagcgaccg tctttctgct gtcgcaaacg gtctcaagct caacggtgtt gattgcgatg      3360
aaggtgagac ttctctcgtc gtgcgtggtc gtcctgacgg taagggtctc ggtaacgctt      3420
ctggagcagc tgtcgctacc cacctcgatc accgtatcgc tatgagcttc ctcgttatgg      3480
```

```
gtctcgtttc tgaaaaccct gttactgttg atgatgctac tatgatcgct actagcttcc    3540
cagagttcat ggatttgatg gctggtcttg gagctaagat cgaactctcc gacactaagg    3600
ctgcttgatg agctcaagaa ttcgagctcg gtaccggatc ctaagatctt aggatcctct    3660
agctagagct ttcgttcgta tcatcggttt cgacaacgtt cgtcaagttc aatgcatcag    3720
tttcattgcg cacacaccag aatcctactg agtttgagta ttatggcatt gggaaaactg    3780
tttttcttgt accatttgtt gtgcttgtaa tttactgtgt tttttattcg gttttcgcta    3840
tcgaactgtg aaatggaaat ggatggagaa gagttaatga atgatatggt ccttttgttc    3900
attctcaaat taatattatt tgttttttct cttatttgtt gtgtgttgaa tttgaaatta    3960
taagagatat gcaaacattt tgttttgagt aaaaatgtgt caaatcgtgg cctctaatga    4020
ccgaagttaa tatgaggagt aaaacacttg tagttgtacc attatgctta ttcactaggc    4080
aacaaatata ttttcagacc tagaaaagct gcaaatgtta ctgaatacaa gtatgtcctc    4140
ttgtgtttta gacatttatg aactttcctt tatgtaattt tccagaatcc ttgtcagatt    4200
ctaatcattg ctttataatt atagttatac tcatggattt gtagttgagt atgaaaatat    4260
tttttaatgc attttatgac ttgccaattg attgacaaca tgcatcaatc gacctgcagc    4320
cactcgaagc ggcccaaccc gggggcctat atggcccggt ccggcggccg cggtacggtc    4380
gactctagag gatccccggc aaaacattt aatacgtatt atttaagaaa aaatatgta    4440 ataatatatt tatattttaa tatctattct tatgtatttt ttaaaaatct attatatatt    4500
gatcaactaa atatttttta tatctacact tattttgcat ttttatcaat tttcttgcgt    4560
tttttggcat atttaataat gactattctt taataatcaa tcattattct tacatggtac    4620
atattgttgg aaccatatga agtgtccatt gcatttgact atgtggatag tgttttgatc    4680
caggcctcca tttgccgctt attaattaat ttggtaacag tccgtactaa tcagttactt    4740
atccttcctc catcataatt aatcttggta gtctcgaatg ccacaacact gactagtctc    4800
ttggatcata agaaaaagcc aaggaacaaa agaagacaaa acacaatgag agtatccttt    4860
gcatagcaat gtctaagttc ataaaattca acaaaaacg caatcacaca cagtggacat    4920
cacttatcca ctagctgatc aggatcgccg cgtcaagaaa aaaaaactgg accccaaaag    4980
ccatgcacaa caacacgtac tcacaaaggt gtcaatcgag cagcccaaaa cattcaccaa    5040
ctcaacccat catgagccca cacatttgtt gtttctaacc caacctcaaa ctcgtattct    5100
cttccgccac ctcatttttg tttatttcaa cacccgtcaa actgcatgcc accccgtggc    5160
caaatgtcca tgcatgttaa caagacctat gactataaat atctgcaatc tcggcccagg    5220
ttttcatcat caagaaccgg gtaccgagct cgagcctagg ggtaaattaa attgtgcctg    5280
catctcggga tatttcatgt ggggttcatc atatttgttg aggaaaagaa actcccgaaa    5340
ttgaattatg catttatata tccttttttca tttctagatt tcctgaaggc ttaggtgtag    5400
gcacctagct agtagctaca atatcagcac ttctctctat tgataaacaa ttggctgtaa    5460
tgccgcagta gaggacgatc acaacatttc gtgctggtta ctttttgttt tatggtcatg    5520
atttcaagac tagacgttct accggagaag cgaccttaga aattcattat ggtggcaaca    5580
gctgctactt catcattttt ccctgttact tcaccctcgc cggactctgg tggagcaggc    5640
agcaaacttg gtggtgggcc tgcaaacctt ggaggactaa aatccaaatc tgcgtcttct    5700
ggtggcttga aggcaaaggc gcaagcccct tcgaaaatta atggaccac agttgttaca    5760 tctaaagaaa gcttcaagca tgatgatgat ctaccttcgc ctcccccag aacttttatc    5820
```

| | |
|---|---|
| aaccagtcct gcaggtttaa actatcagtg tttgaaaatg gcttcatgtc cgggaaatct | 5880 |
| acatggatca gcaaaggtag atcatcatca tgcttgaagc tttctttaga tgtaacaact | 5940 |
| gtggttccat taattttcga aggggcttgc gcctttgcct tcaagccacc agaagacgca | 6000 |
| gatttggatt ttagtcctcc aaggtttgca ggcccaccac caagtttgct gcctgctcca | 6060 |
| ccagagtccg gcgagggtga agtaacaggg aaaaatgatg aagtagcagc tgttgccacc | 6120 |
| ataatgaatt tctaaggtcg cttctccggt agaacgtcta gtcttgaaat catgaccata | 6180 |
| aaacaaaaag taaccagcac gaaatgttgt gatcgtcctc tactgcggca ttacagccaa | 6240 |
| ttgtttatca atagagagaa gtgctgatat tgtagctact agctaggtgc ctacacctaa | 6300 |
| gccttcagga aatctagaaa tgaaaaagga tatataaatg cataattcaa tttcgggagt | 6360 |
| ttcttttcct caacaaatat gatgaacccc acatgaaata tcccgagatg caggcacaat | 6420 |
| ttaatttacc cctaggacgc gtaacaaaag agtgcctcac atttgatgca atagctctgt | 6480 |
| aatgtttcat tcatttgctt atttcggcct tgttttctc gtattctatg ggctgatgtc | 6540 |
| tcatatggga cttttctact agagagccta cgttacttta ccattatatt gtattctttg | 6600 |
| agacattatt attattttt tacctttga ggacactctt tttttgtatt tgaaggaatt | 6660 |
| tattgtttat tttgtttgga atatgtttgg ttggatttat tcgattcata tatattat | 6720 |
| aaaagtaatt atgttattaa gaaacgtagt aagaacttac aaatataagg atcgaatccc | 6780 |
| gaacttcatg caaatcaatt tacaacccac acaagtttaa cattaaatta acgtgattgg | 6840 |
| ttagtaaatt catgtttctc tgtttaattt gttgaatttg tacattataa gggcgaattc | 6900 |
| tgcagatatc catcacactg gcggccgcgg gtcccatata tatatagcga tcgcggcgcg | 6960 |
| ccaaatcgtg aagtttctca tctaagcccc catttggacg tgaatgtaga cacgtcgaaa | 7020 |
| taaagatttc cgaattagaa taatttgttt attgctttcg cctataaata cgacggatcg | 7080 |
| taatttgtcg ttttatcaaa atgtactttc attttataat aacgctgcgg acatctacat | 7140 |
| ttttgaattg aaaaaaaatt ggtaattact cttttctttt ctccatattg accatcatac | 7200 |
| tcattgctga tccatgtaga tttcccggac atgaagccat ttacaattga a | 7251 |

```
<210> SEQ ID NO 6
<211> LENGTH: 13224
<212> TYPE: DNA
<213> ORGANISM: Artificial Sequence
<220> FEATURE:
<223> OTHER INFORMATION: Contig
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (125)..(125)
<223> OTHER INFORMATION: n is a, c, g, or t
<220> FEATURE:
<221> NAME/KEY: misc_feature
<222> LOCATION: (729)..(729)
<223> OTHER INFORMATION: n is a, c, g, or t
<220> FEATURE:
<221> NAME/KEY: misc_feature
<222> LOCATION: (855)..(855)
<223> OTHER INFORMATION: n is a, c, g, or t
<220> FEATURE:
<221> NAME/KEY: misc_feature
<222> LOCATION: (1203)..(1203)
<223> OTHER INFORMATION: n is a, c, g, or t
<220> FEATURE:
<221> NAME/KEY: misc_feature
<222> LOCATION: (1243)..(1243)
<223> OTHER INFORMATION: n is a, c, g, or t
```

```
<220> FEATURE:
<221> NAME/KEY: misc_feature
<222> LOCATION: (1522)..(1522)
<223> OTHER INFORMATION: n is a, c, g, or t

<400> SEQUENCE: 6
actatagggc acgcgtggtc gacggnccgg gctggtaaac ttaacaaagc cttatatgga      60
cttaaacaag cttccaaagc ttggtatgga aaactaagtt catttatttt ggaaaatggc     120
tttgnacatg aatggtcga cacaacactc tttcctaaga attatgattc tcaattttta     180
ttagtacaag tgtatgtgga tgatatcatt tttggtgcta ctaatgaaat gctctatgaa     240
gattttctta agtaatgca aactgagttt gaaatgagca tgatgggaga gctaaaattc     300
ttccttggac tgcaaataaa gcaaacaccc caaggcattt acattcatca gaccaagtat     360
gtgaaaaatt agttgaagaa gttcaacata agtgatgaaa aagagatgaa gacttttatg     420
catcccacta cacatcttgg actggatgag aatcaatga aggtggacgt gactcaatac      480
aaagcaatga ttggatcact gctctatctt aatgcttcta ggccttatat aatttttagt     540
gttttattat gtgcaagatt ccaaaaggaa ccaagggaag ttcatttaac tgcagttaaa     600
cctatattct aatatttaat tagaactcat aaccttggtc ttatgcttaa gagaagagat     660
agtttcagac tcatgagcta ttgagatgtg gactatgttg gtgataaagt cgaaagaaaa     720
agtacaagng gaagttgtca ctttataggt ggcaacttag tcacttggat atggaagaag     780
tagggatcaa ctacattgtt cactgctgaa gtagaatgcg tgtcagtagc catggaggtt     840
accctcgaca ttgangaccc caagaaatag gttcaaagtt ttggaaatcc acagggtcag     900
agcacaagtg caagtttcaa gtatcaaggc agcaacgaag ctatatcgta ggtaggggag     960
tttagtggta ccaataatgc ccaaacaccc actggtggga ctcaaaatct acaaggggag    1020
agcagaatgt cttctacatc atcaatatcc aaaccaagat tctcaagacc gtgaaacaaa    1080
ggatctcagg gtgttgttat cactgcggtt tggccttttgg gccaaggcac tgttgtcctg    1140
aaaaaaatat gagagttgta atactcgcta aggatgagta gattaatgaa gacggggaga    1200
tcntaggatt aaaaaatgag aatgaggaag aatgtgagga agntttggag atggtttgct    1260
agcggatgga tttgtcagtt tgttccgcag gtgggctaac ccagcctcaa gcatgaagct    1320
taggtgagaa ttatagggggc aagaggtgat aatcttgatt gacaataggg caagccacaa    1380
ctttatatcc aacaaattgg tacataaatt gggactcagc atagatccca caaagcccta    1440
ttatatgaga ttggggggata gtaaccgcaa atccactcaa ggatgttgta agaacttaaa    1500
aaaatagttgg gagcttatac cntggtagga tatttctatc tatttaagtt gggaggagtg    1560
gacctaatta ttggagttgc ttagttggaa acattgggag aaattaaggt gaattggagg    1620
accctaagta tgtctttttgt ccaccaagat cagaatatgg tgatcaagga gatcttggtt    1680
tattgaagac aatgatcatt ttgagaacat tgcaaaaaat agttagcaag gaagttgaga    1740
tgatgttcat gttgtgggta attgaaagca actatgtgga acaaattgat ttaacaaaga    1800
accaagaaaa ttagttgtag caagtactga tagagtttgc tacagttttt caggacctaa    1860
gggtttacca ccatctagag aggttgatca caagattgca attaagtccg gggcatatcc    1920
agataatgtt aggccttatc gttaccccca cttacagaag aatgagataa aaactctagt    1980
ggttgagatg ttatgattgg ggattattag actaagcaat agctcctatt ctagcccagt    2040
aattttggta aaaaggaaag atggaagttg acgattatgt atggattatc aggctttaag    2100
taaggctaca gtcccagaca agttcctgat tcctgtcatg aaagagttgt tggatgagtt    2160
```

```
aaatggaccc atccacttct ctaaaataga tctaaaggca aggtatcacc aaatcagaat      2220
gcacaaacct accttcagaa ctcaccaagg acattatgaa tctccagtga tgccatttgg      2280
attaacaaac accccgacca cgttccaatg agctatgaat gccacactga aaccgttcct      2340
tcgtaggtat gtggtagtgt tcttgatga cattttggtc tatagtaagt cttgggaagc      2400
ccatttggat catttgagtt aggtgttggc caggttatta gaacattatt tcttcacaaa      2460
tgtttttaaa aaaaatgta gttttggtca aattaaggcg ggttgcttag ggcacgttat      2520
ctctaaagaa ggagttttga tgaggccatt ttgtagtggc caatgcctaa aactcctaag      2580
tctttgagag ggttttttgga acttacaggt tattataaaa ggtccatttg caattatggg     2640
aagatagctc gcccattgat tgatctatta agtaaggaa attttaagtg gaatgaggat      2700
agtattaagg cttccataca attacaacaa gctattacca caataccaac actatccatg      2760 cttgatttt caaacaatt ctccatagaa tgtgatgcct cggggaaggg aattggagtt       2820
gttctaacac aagatagaaa gcaaattgct tatttcaaca aggcattaaa agatttgact      2880 cttttctaaat ctatgtatga aaaggaatca atggctcttg tcttagccat acaacattgg    2940
aggccttatc ttccggatta gaaatttact atatacattg accaaaaaag tttgagatat      3000
ctactagatc agcgaattac aactcaacca acaatattgg gtagccaagt tgctggggta     3060
tgagtttgac attgtgtata aggtgggggc ttcaaacaag gttgttgatg ctctatctag     3120
aagagatgaa gacaaagaat tgcagggcat ttctagacct ttctggaaag acataacaaa    3180
aattaatgaa gaagttcaga aggatcccgc gttggctaaa atccgagaag aattgaagga    3240
taatctagat tcacaccctc agtacaccct ggagtgtgac atattatact tcagagggag    3300
gttggtccta ttagcttctt cattgtggat tccaaagtta ctacaagaat tccagacttc    3360
tcttatggga gggcactcgg gtatttacat aacttataga agaatcactc aatcgcttta    3420
ttggatacca ataaagggag aaatcactaa gtttgtggtt catgtccggg aaatctacat    3480
ggatcagcaa tgagtatgat ggtcaatatg gagaaaaga aagagtaatt accaatttt     3540 tttcaattca aaaatgtaga tgtccgcagc gttattataa aatgaaagta cattttgata    3600
aaacgacaaa ttacgatccg tcgtatttat aggcgaaagc aataaacaaa ttattctaat    3660
tcggaaatct ttatttcgac gtgtctacat tcacgtccaa atggggggctt agatgagaaa   3720 cttcacgatc gatgcggccg tcgagtggaa gctaattctc agtccaaagc ctcaacaagg    3780
tcagggtaca gagtctccaa accattagcc aaaagctaca ggagatcaat gaagaatctt    3840
caatcaaagt aaactactgt tccagcacat gcatcatggt cagtaagttt cagaaaaaga    3900
catccaccga agacttaaag ttagtgggca tctttgaaag taatcttgtc aacatcgagc    3960
agctggcttg tggggaccag acaaaaaagg aatggtgcag aattgttagg cgcacctacc    4020
aaaagcatct ttgcctttat tgcaaagata aagcagattc ctctagtaca agtggggaac    4080
aaaataacgt ggaaaagagc tgtcctgaca gcccactcac taatgcgtat gacgaacgca    4140
gtgacgacca caaagaatt agcttgagct caggatttag cagcattcca gattgggttc     4200
aatcaacaag gtacgagcca tatcacttta ttcaaattgg tatcgccaaa accaagaagg    4260
aactcccatc ctcaaaggtt tgtaaggaag aattcgatat caagcttgat atcggaagtt    4320
tctctcttga gggaggttgc tcgtggaatg ggacacatat ggttgttata ataaaccatt     4380
tccattgtca tgagattttg aggttaatat atactttact tgttcattat tttatttggt     4440
gtttgaataa atgatataaa tggctcttga taatctgcat tcattgagat atcaaatatt    4500
tactctagag aagagtgtca tatagattga tggtccacaa tcaatgaaat ttttgggaga    4560
```

```
cgaacatgta taaccatttg cttgaataac cttaattaaa aggtgtgatt aaatgatgtt    4620
tgtaacatgt agtactaaac attcataaaa cacaaccaac ccaagaggta ttgagtattc    4680
acggctaaac aggggcataa tggtaattta agaatgata ttattttatg ttaaacccta    4740
acattggttt cggattcaac gctataaata aaaccactct cgttgctgat tccatttatc    4800
gttcttattg accctagccg ctacacactt ttctgcgata tctctgaggt aagcgttaac    4860
gtacccttag atcgttcttt ttcttttcg tctgctgatc gttgctcata ttatttcgat    4920
gattgttgga ttcgatgctc tttgttgatt gatcgttctg aaaattctga tctgttgttt    4980
agattttatc gattgttaat atcaacgttt cactgcttct aaacgataat ttattcatga    5040
aactattttc ccattctgat cgatcttgtt ttgagatttt aatttgttcg attgattgtt    5100
ggttggtgga tctatatacg agtgaacttg ttgatttgcg tatttaagat gtatgtcgat    5160
ttgaattgtg attgggtaat tctggagtag cataacaaat ccagtgttcc cttttctaa    5220 gggtaattct cggattgttt gcttatatc tcttgaaatt gccgatttga ttgaatttag    5280
ctcgcttagc tcagatgata gagcaccaca attttttgtgg tagaaatcgg tttgactccg    5340
atagcggctt tttactatga ttgttttgtg ttaaagatga ttttcataat ggttatatat    5400
gtctactgtt tttattgatt caatatttga ttgttctttt ttttgcagat ttgttgacca    5460
gagatctacc atggcgcaag ttagcagaat ctgcaatggt gtgcagaacc catctcttat    5520
ctccaatctc tcgaaatcca gtcaacgcaa atctcccttt tcggtttctc tgaagacgca    5580
gcagcatcca cgagcttatc cgatttcgtc gtcgtgggga ttgaagaaga gtgggatgac    5640
gttaattggc tctgagcttc gtcctcttaa ggtcatgtct tctgtttcca cggcgtgcat    5700
gcttcacggt gcaagcagcc gtccagcaac tgctcgtaag tcctctggtc tttctggaac    5760
cgtccgtatt ccaggtgaca agtctatctc ccacaggtcc ttcatgtttg gaggtctcgc    5820
tagcggtgaa actcgtatca ccggtctttt ggaaggtgaa gatgttatca acactggtaa    5880
ggctatgcaa gctatgggtg ccagaatccg taaggaaggt gatacttgga tcattgatgg    5940
tgttggtaac ggtggactcc ttgctcctga ggctcctctc gatttcggta acgctgcaac    6000
tggttgccgt ttgactatgg gtcttgttgg tgtttacgat ttcgatagca ctttcattgg    6060
tgacgcttct ctcactaagc gtccaatggg tcgtgtgttg aacccacttc gcgaaatggg    6120
tgtgcaggtg aagtctgaag acggtgatcg tcttccagtt accttgcgtg gaccaaagac    6180
tccaacgcca atcacctaca gggtacctat ggcttccgct caagtgaagt ccgctgttct    6240
gcttgctggt ctcaacaccc caggtatcac cactgttatc gagccaatca tgactcgtga    6300
ccacactgaa aagatgcttc aaggttttgg tgctaacctt accgttgaga ctgatgctga    6360
cggtgtgcgt accatccgtc ttgaaggtcg tggtaagctc accggtcaag tgattgatgt    6420
tccaggtgat ccatcctcta ctgctttccc attggttgct gccttgcttg ttccaggttc    6480
cgacgtcacc atccttaacg ttttgatgaa cccaacccgt actggtctca tcttgactct    6540
gcaggaaatg ggtgccgaca tcgaagtgat caacccacgt cttgctggtg agaagacgt    6600 ggctgacttg cgtgttcgtt cttctacttt gaagggtgtt actgttccag aagaccgtgc    6660
tccttctatg atcgacagt atccaattct cgctgttgca gctgcattcg ctgaaggtgc    6720
taccgttatg aacggtttgg aagaactccg tgttaaggaa agcgaccgtc tttctgctgt    6780
cgcaaacggt ctcaagctca acggtgttga ttgcgatgaa ggtgagactt ctctcgtcgt    6840
gcgtggtcgt cctgacggta agggtctcgg taacgcttct ggagcagctg tcgctaccca    6900
```

```
cctcgatcac cgtatcgcta tgagcttcct cgttatgggt ctcgtttctg aaaaccctgt   6960
tactgttgat gatgctacta tgatcgctac tagcttccca gagttcatgg atttgatggc   7020
tggtcttgga gctaagatcg aactctccga cactaaggct gcttgatgag ctcaagaatt   7080
cgagctcggt accggatcct aagatcttag gatcctctag ctagagcttt cgttcgtatc   7140
atcggtttcg acaacgttcg tcaagttcaa tgcatcagtt tcattgcgca cacaccagaa   7200
tcctactgag tttgagtatt atggcattgg gaaaactgtt tttcttgtac catttgttgt   7260
gcttgtaatt tactgtgttt tttattcggt tttcgctatc gaactgtgaa atggaaatgg   7320
atggagaaga gttaatgaat gatatggtcc ttttgttcat tctcaaatta atattatttg   7380 tttttctct tatttgttgt gtgttgaatt tgaaattata agagatatgc aaacattttg   7440
ttttgagtaa aaatgtgtca atcgtggcc tctaatgacc gaagttaata tgaggagtaa   7500
aacacttgta gttgtaccat tatgcttatt cactaggcaa caaatatatt ttcagaccta   7560
gaaaagctgc aaatgttact gaatacaagt atgtcctctt gtgttttaga catttatgaa   7620
ctttccttta tgtaattttc cagaatcctt gtcagattct aatcattgct ttataattat   7680
agttatactc atggatttgt agttgagtat gaaaatattt tttaatgcat tttatgactt   7740
gccaattgat tgacaacatg catcaatcga cctgcagcca ctcgaagcgg cccaacccgg   7800
gggcctatat ggcccggtcc ggcggccgcg gtacggtcga ctctagagga tccccggcaa   7860
aaacatttaa tacgtattat ttaagaaaaa aatatgtaat aatatattta tattttaata   7920
tctattctta tgtatttttt aaaaatctat tatatattga tcaactaaaa tattttata   7980 tctacactta ttttgcattt ttatcaattt tcttgcgttt tttggcatat ttaataatga   8040
ctattcttta ataatcaatc attattctta catggtacat attgttggaa ccatatgaag   8100
tgtccattgc atttgactat gtggatagtg ttttgatcca ggcctccatt tgccgcttat   8160
taattaattt ggtaacagtc cgtactaatc agttacttat ccttcctcca tcataattaa   8220
tcttggtagt ctcgaatgcc acaacactga ctagtctctt ggatcataag aaaaagccaa   8280
ggaacaaaag aagacaaaac acaatgagag tatcctttgc atagcaatgt ctaagttcat   8340
aaaattcaaa caaaaacgca atcacacaca gtggacatca cttatccact agctgatcag   8400
gatcgccgcg tcaagaaaaa aaaactggac cccaaaagcc atgcacaaca acacgtactc   8460 acaaggtgt caatcgagca gcccaaaaca ttcaccaact caaccatca tgagcccaca   8520 catttgttgt ttctaaccca acctcaaact cgtattctct tccgccacct cattttttgtt   8580 tatttcaaca cccgtcaaac tgcatgccac cccgtggcca aatgtccatg catgttaaca   8640
agacctatga ctataaatat ctgcaatctc ggcccaggtt ttcatcatca agaaccgggt   8700
accgagctcg agcctagggg taaattaaat tgtgcctgca tctcgggata tttcatgtgg   8760
ggttcatcat atttgttgag gaaaagaaac tcccgaaatt gaattatgca tttatatatc   8820 cttttttcatt tctagatttc ctgaaggctt aggtgtaggc acctagctag tagctacaat   8880
atcagcactt ctctctattg ataaacaatt ggctgtaatg ccgcagtaga ggacgatcac   8940
aacatttcgt gctggttact ttttgttttta tggtcatgat tcaagacta gacgttctac   9000 cggagaagcg accttagaaa ttcattatgg tggcaacagc tgctacttca tcattttcc   9060 ctgttacttc accctcgccg gactctggtg gagcaggcag caaacttggt ggtgggcctg   9120
caaaccttgg aggactaaaa tccaaatctg cgtcttctgg tggcttgaag gcaaaggcgc   9180
aagccccttc gaaaattaat ggaaccacag ttgttcatcc taaagaaagc ttcaagcatg   9240
atgatgatct accttcgcct cccccccagaa cttttatcaa ccagtcctgc aggtttaaac   9300
```

```
tatcagtgtt tgaaaatggc ttcatgtccg ggaaatctac atggatcagc aaaggtagat   9360
catcatcatg cttgaagctt tctttagatg taacaactgt ggttccatta attttcgaag   9420
gggcttgcgc cttttgcctt caagccaccag aagacgcaga tttggatttt agtcctccaa   9480
ggtttgcagg cccaccacca agtttgctgc ctgctccacc agagtccggc gagggtgaag   9540
taacagggaa aaatgatgaa gtagcagctg ttgccaccat aatgaatttc taaggtcgct   9600
tctccggtag aacgtctagt cttgaaatca tgaccataaa acaaaaagta accagcacga   9660
aatgttgtga tcgtcctcta ctgcggcatt acagccaatt gtttatcaat agagagaagt   9720
gctgatattg tagctactag ctaggtgcct acacctaagc cttcaggaaa tctagaaatg   9780
aaaaaggata tataaatgca taattcaatt tcgggagttt cttttcctca acaaatatga   9840
tgaaccccac atgaaatatc ccgagatgca ggcacaattt aatttacccc taggacgcgt   9900
aacaaaagag tgcctcacat ttgatgcaat agctctgtaa tgtttcattc atttgcttat   9960
ttcggccttg ttttctcgt attctatggg ctgatgtctc atatgggact tttctactag  10020
agagcctacg ttactttacc attatattgt attctttgag acattattat tatttttta  10080 ccttttgagg acactctttt tttgtatttg aaggaattta ttgtttattt tgtttggaat  10140
atgtttggtt ggatttattc gattcatata tattatataa aagtaattat gttattaaga  10200
aacgtagtaa gaactacaa atataaggat cgaatcccga acttcatgca atcaattta  10260 caacccacac aagtttaaca ttaaattaac gtgattggtt agtaaattca tgtttctctg  10320
tttaatttgt tgaatttgta cattataagg gcgaattctg cagatatcca tcacactggc  10380
ggccgcgggt cccatatata tatagcgatc gcggcgcgcc aaatcgtgaa gtttctcatc  10440
taagccccca tttggacgtg aatgtagaca cgtcgaaata aagatttccg aattagaata  10500
atttgtttat tgctttcgcc tataaatacg acggatcgta atttgtcgtt ttatcaaaat  10560
gtactttcat tttataataa cgctgcggac atctacattt ttgaattgaa aaaaaattgg  10620
taattactct ttcttttttct ccatattgac catcatactc attgctgatc catgtagatt  10680
tcccggacat gaagccattt acaattgaag agactcaggg tgttgttatc actgcggttt  10740
ggcctttggg ccaaggcacc gttgtcctga aaaaatatg agagttgtaa tactcgctaa  10800
ggatgagtag attaatgaag acggggagat cataggatta aaaatgaga atgaggaaga  10860 atgtgaggaa gttttggaga tggtttgcta gcggatggat ttgtcagttt gttccgcagg  10920
tgggctaacc cagcctcaag catgaagctt aggtgagaat tatagggca agaggtgata  10980 atcttgattg acaatagggc aagccacaac tttatatcca acaaattggt acataaattg  11040
ggactcagca tagatcccac aaagccctat tatatgagat tgggggatag taaccgcaaa  11100
tccactcaag gatgttgtaa gaacttaaaa aatagttggg agcttatacc atggtaggat  11160
atttctatct atttaagttg ggaggagtgg acctaattat tggagttgct tagttggaaa  11220
cattgggaga aattaaggtg aattggagga ccctaagtat gtcttttgtc caccaagatc  11280
agaatatggt gatcaaggag atcttggttt attgaagaca atgatcattt tgagaacatt  11340
gcaaaaaata gttagcaagg aagttgagat gatgttcatg ttgtgggtaa ttgaaagcaa  11400
ctatgtggaa caaattgatt taacaaagaa ccaagaaaat tagttgtagc aagtactgat  11460
agagtttgct acagttttc aggacctaag ggtttaccac catctagaga ggttgatcac  11520
aagattgcaa ttaagtccgg ggcatatcca gataatgtta ggccttatcg ttaccccac  11580 ttacagaaga atgagataaa aactctagtg gttgagatgt tatgattggg gattattaga  11640
```

```
ctaagcaata gctcctattc tagcccagta attttggtaa aaaggaaaga tggaagttga    11700
cgattatgta tggattatca ggctttaagt aaggctacag tcccagacaa gttcctgatt    11760
cctgtcatga aagagttgtt ggatgagtta aatggaccca tccacttctc taaaatagat    11820
ctaaaggcaa ggtatcacca aatcagaatg cacaaaccta ccttcagaac tcaccaagga    11880
cattatgaat ctccagtgat gccatttgga ttaacaaaca ccccgaccac gttccaatga    11940
gctatgaatg ccacactgaa accgttcctt cgtaggtatg tggtagtgtt ctttgatgac    12000
attttggtct atagtaagtc ttgggaagcc catttggatc atttgagtta ggtgttggcc    12060
aggttattag aacattattt cttcacaaat gtttttaaaa aaaatgtag ttttggtcaa    12120 attaaggcgg gttgcttagg gcacgttatc tctaaagaag gagttttgat gaggccattt    12180
tgtagtggcc aatgcctaaa actcctaaga ctttgagagg gttttggaa cttacaggtt    12240 attataaaag gtccatttgc aattatggga agatagctcg cccattgatt gatctattaa    12300
agtaaggaaa ttttaagtgg aatgaggata gtattaaggc ttccatacaa ttacaacaag    12360
ctattaccac aataccaaca ctatccatgc ttgattttc aaaacaattc tccatagaat    12420
gtgatgcctc ggggaaggga attggagttg ttctaacaca agatagaaag caaattgctt    12480
atttcaacaa ggcattaaaa gatttgactc tttctaaatc tatgtatgaa aaggaatcaa    12540
tggctcttgt cttagccata caacattgga ggccttatct tccggattag aaatttacta    12600
tatacattga ccaaaaaagt ttgagatatc tactagatca gcgaattaca actcaaccaa    12660
caatattggg tagccaagtt gctggggtat gagtttgaca ttgtgtataa ggtggggct    12720 tcaaacaagg ttgttgatgc tctatctaga agagatgaag acaaagaatt gcagggcatt    12780
tctagacctt tctggaaaga cataacaaaa attaatgaag aagttcagaa ggatcccgcg    12840
ttggctaaaa tccgagaaga attgaaggat aatctagatt cacaccctca gtacaccctg    12900
gagtgtgaca tattatactt cagagggagg ttggtcctat tagcttcttc attgtggatt    12960
ccaaagttac tacaagaatt ccagacttct cttatgggag ggcactcggg tatttacata    13020
acttatagaa gaatcactca atcgctttat tggataccaa taagggaga aatcactaag    13080 tttgtggttg cgtgtcatgt gggccaaaga agtaaatatc aagcatcctc tccagcaggt    13140
ttactacaac ctttgccaat tccaaatgct atttgggaag aaattagtat gaatttatt    13200 gtaggtatgc taaaatcaaa aggg                                         13224

<210> SEQ ID NO 7
<211> LENGTH: 6583
<212> TYPE: DNA
<213> ORGANISM: Artificial Sequence
<220> FEATURE:
<223> OTHER INFORMATION: Cassettes

<400> SEQUENCE: 7
aattctcagt ccaaagcctc aacaaggtca gggtacagag tctccaaacc attagccaaa      60
agctacagga gatcaatgaa gaatcttcaa tcaaagtaaa ctactgttcc agcacatgca     120
tcatggtcag taagtttcag aaaaagacat ccaccgaaga cttaaagtta gtgggcatct     180
ttgaaagtaa tcttgtcaac atcgagcagc tggcttgtgg ggaccagaca aaaaaggaat     240
ggtgcagaat tgttaggcgc acctaccaaa agcatctttg cctttattgc aaagataaag     300
cagattcctc tagtacaagt ggggaacaaa ataacgtgga aaagagctgt cctgacagcc     360
cactcactaa tgcgtatgac gaacgcagtg acgaccacaa aagaattagc ttgagctcag     420
gatttagcag cattccagat tgggttcaat caacaaggta cgagccatat cactttattc     480
```

```
aaattggtat cgccaaaacc aagaaggaac tcccatcctc aaaggtttgt aaggaagaat    540
tcgatatcaa gcttgatatc ggaagtttct ctcttgaggg aggttgctcg tggaatggga    600
cacatatggt tgttataata aaccatttcc attgtcatga gattttgagg ttaatatata    660
ctttacttgt tcattatttt atttggtgtt tgaataaatg atataaatgg ctcttgataa    720
tctgcattca ttgagatatc aaatatttac tctagagaag agtgtcatat agattgatgg    780
tccacaatca atgaaatttt tgggagacga acatgtataa ccatttgctt gaataacctt    840
aattaaaagg tgtgattaaa tgatgtttgt aacatgtagt actaaacatt cataaaacac    900
aaccaaccca agaggtattg agtattcacg gctaaacagg ggcataatgg taatttaaag    960
aatgatatta ttttatgtta aaccctaaca ttggtttcgg attcaacgct ataaataaaa    1020
ccactctcgt tgctgattcc atttatcgtt cttattgacc ctagccgcta cacacttttc    1080
tgcgatatct ctgaggtaag cgttaacgta cccttagatc gttcttttc tttttcgtct     1140 gctgatcgtt gctcatatta tttcgatgat tgttggattc gatgctcttt gttgattgat    1200
cgttctgaaa attctgatct gttgtttaga ttttatcgat tgttaatatc aacgtttcac    1260
tgcttctaaa cgataattta ttcatgaaac tatttttccca ttctgatcga tcttgttttg    1320
agattttaat ttgttcgatt gattgttggt tggtggatct atatacgagt gaacttgttg    1380
atttgcgtat ttaagatgta tgtcgatttg aattgtgatt gggtaattct ggagtagcat    1440
aacaaatcca gtgttccctt tttctaaggg taattctcgg attgtttgct ttatatctct    1500
tgaaattgcc gatttgattg aatttagctc gcttagctca gatgatagag caccacaatt    1560
tttgtggtag aaatcggttt gactccgata gcggcttttt actatgattg ttttgtgtta    1620
aagatgattt tcataatggt tatatatgtc tactgttttt attgattcaa tatttgattg    1680 ttctttttt tgcagatttg ttgaccagag atctaccatg gcgcaagtta gcagaatctg     1740
caatggtgtg cagaacccat ctcttatctc caatctctcg aaatccagtc aacgcaaatc    1800
tcccttatcg gtttctctga agacgcagca gcatccacga gcttatccga tttcgtcgtc    1860
gtggggattg aagaagagtg ggatgacgtt aattggctct gagcttcgtc ctcttaaggt    1920
catgtcttct gtttccacgg cgtgcatgct tcacggtgca agcagccgtc cagcaactgc    1980
tcgtaagtcc tctggtcttt ctggaaccgt ccgtattcca ggtgacaagt ctatctccca    2040
caggtccttc atgtttggag gtctcgctag cggtgaaact cgtatcaccg gtcttttgga    2100
aggtgaagat gttatcaaca ctggtaaggc tatgcaagct atgggtgcca gaatccgtaa    2160
ggaaggtgat acttggatca ttgatggtgt tggtaacggt ggactccttg ctcctgaggc    2220
tcctctcgat ttcggtaacg ctgcaactgg ttgccgtttg actatgggtc ttgttggtgt    2280
ttacgatttc gatagcactt tcattggtga cgcttctctc actaagcgtc caatgggtcg    2340
tgtgttgaac ccacttcgcg aaatgggtgt gcaggtgaag tctgaagacg gtgatcgtct    2400
tccagttacc ttgcgtggac caaagactcc aacgccaatc acctcagggg tacctatggc    2460
ttccgctcaa gtgaagtccg ctgttctgct tgctggtctc aacaccccag gtatcaccac    2520
tgttatcgag ccaatcatga ctcgtgacca cactgaaaag atgcttcaag gttttggtgc    2580
taaccttacc gttgagactg atgctgacgg tgtgcgtacc atccgtcttg aaggtcgtgg    2640
taagctcacc ggtcaagtga ttgatgttcc aggtgatcca tcctctactg ctttcccatt    2700
ggttgctgcc ttgcttgttc caggttccga cgtcaccatc cttaacgttt tgatgaaccc    2760
aacccgtact ggtctcatct tgactctgca ggaaatgggt gccgacatcg aagtgatcaa    2820
```

```
cccacgtctt gctggtggag aagacgtggc tgacttgcgt gttcgttctt ctactttgaa    2880
gggtgttact gttccagaag accgtgctcc ttctatgatc gacgagtatc caattctcgc    2940
tgttgcagct gcattcgctg aaggtgctac cgttatgaac ggtttggaag aactccgtgt    3000
taaggaaagc gaccgtcttt ctgctgtcgc aaacggtctc aagctcaacg tgttgattg     3060 cgatgaaggt gagacttctc tcgtcgtgcg tggtcgtcct gacggtaagg gtctcggtaa    3120
cgcttctgga gcagctgtcg ctacccacct cgatcaccgt atcgctatga gcttcctcgt    3180
tatgggtctc gtttctgaaa accctgttac tgttgatgat gctactatga tcgctactag    3240
cttcccagag ttcatggatt tgatggctgg tcttggagct aagatcgaac tctccgacac    3300
taaggctgct tgatgagctc aagaattcga gctcggtacc ggatcctaag atcttaggat    3360
cctctagcta gagctttcgt tcgtatcatc ggtttcgaca acgttcgtca agttcaatgc    3420
atcagtttca ttgcgcacac accagaatcc tactgagttt gagtattatg gcattgggaa    3480
aactgttttt cttgtaccat tgttgtgct tgtaatttac tgtgttttt attcggtttt       3540 cgctatcgaa ctgtgaaatg gaaatggatg gagaagagtt aatgaatgat atggtccttt    3600
tgttcattct caaattaata ttatttgttt tttctcttat ttgttgtgtg ttgaatttga    3660
aattataaga gatatgcaaa cattttgttt tgagtaaaaa tgtgtcaaat cgtggcctct    3720
aatgaccgaa gttaatatga ggagtaaaac acttgtagtt gtaccattat gcttattcac    3780
taggcaacaa atatattttc agacctagaa aagctgcaaa tgttactgaa tacaagtatg    3840
tcctcttgtg ttttagacat ttatgaactt tcctttatgt aattttccag aatccttgtc    3900
agattctaat cattgcttta taattatagt tatactcatg gatttgtagt tgagtatgaa    3960
aatatttttt aatgcatttt atgacttgcc aattgattga caacatgcat caatcgacct    4020
gcagccactc gaagcggccc aacccggggg cctatatggc ccggtccggc ggccgcggta    4080
cggtcgactc tagaggatcc ccggcaaaaa catttaatac gtattattta agaaaaaaat    4140
atgtaataat atatttatat tttaatatct attcttatgt attttttaaa aatctattat    4200
atattgatca actaaaatat tttatatct acacttattt tgcatttta tcaattttct      4260 tgcgtttttt ggcatattta ataatgacta ttctttaata atcaatcatt attcttacat    4320
ggtacatatt gttggaacca tatgaagtgt ccattgcatt tgactatgtg gatagtgttt    4380
tgatccaggc ctccatttgc cgcttattaa ttaatttggt aacagtccgt actaatcagt    4440
tacttatcct tcctccatca taattaatct tggtagtctc gaatgccaca cactgactag   4500
gtctcttgga tcataagaaa aagccaagga acaaaagaag acaaaacaca atgagagtat    4560
cctttgcata gcaatgtcta agttcataaa attcaaacaa aaacgcaatc acacacagtg    4620
gacatcactt atccactagc tgatcaggat cgccgcgtca agaaaaaaaa actgaccccc    4680
aaaagccatg cacaacaaca cgtactcaca aaggtgtcaa tcgagcagcc caaaacattc    4740
accaactcaa cccatcatga gcccacacat ttgttgtttc taacccaacc tcaaactcgt    4800
attctcttcc gccacctcat ttttgtttat ttcaacaccc gtcaaactgc atgccacccc    4860
gtggccaaat gtccatgcat gttaacaaga cctatgacta taaatatctg caatctcggc    4920
ccaggttttc atcatcaaga accgggtacc gagctcgagc ctaggggtaa attaaattgt    4980
gcctgcatct cgggatattt catgtggggt tcatcatatt tgttgaggaa aagaaactcc    5040
cgaaattgaa ttatgcattt atatatcctt tttcatttct agatttcctg aaggcttagg    5100
tgtaggcacc tagctagtag ctacaatatc agcacttctc tctattgata aacaattggc    5160
tgtaatgccg cagtagagga cgatcacaac atttcgtgct ggttacttt tgttttatgg     5220
```

-continued

```
tcatgatttc aagactagac gttctaccgg agaagcgacc ttagaaattc attatggtgg    5280
caacagctgc tacttcatca ttttccctg ttacttcacc ctcgccggac tctggtggag     5340
caggcagcaa acttggtggt gggcctgcaa accttggagg actaaaatcc aaatctgcgt    5400
cttctggtgg cttgaaggca aaggcgcaag ccccttcgaa aattaatgga accacagttg    5460
ttacatctaa agaaagcttc aagcatgatg atgatctacc ttcgcctccc cccagaactt    5520
ttatcaacca gtcctgcagg tttaaactat cagtgtttga aaatggcttc atgtccggga    5580
aatctacatg gatcagcaaa ggtagatcat catcatgctt gaagctttct ttagatgtaa    5640
caactgtggt tccattaatt ttcgaagggg cttgcgcctt tgccttcaag ccaccagaag    5700
acgcagattt ggattttagt cctccaaggt ttgcaggccc accaccaagt ttgctgcctg    5760
ctccaccaga gtccggcgag ggtgaagtaa cagggaaaaa tgatgaagta gcagctgttg    5820
ccaccataat gaatttctaa ggtcgcttct ccggtagaac gtctagtctt gaaatcatga    5880
ccataaaaca aaaagtaacc agcacgaaat gttgtgatcg tcctctactg cggcattaca    5940
gccaattgtt tatcaataga gagaagtgct gatattgtag ctactagcta ggtgcctaca    6000
cctaagcctt caggaaatct agaaatgaaa aaggatatat aaatgcataa ttcaatttcg    6060
ggagtttctt ttcctcaaca aatatgatga accccacatg aaatatcccg agatgcaggc    6120
acaatttaat ttaccctag gacgcgtaac aaaagagtgc ctcacatttg atgcaatagc     6180
tctgtaatgt ttcattcatt tgcttatttc ggccttgttt ttctcgtatt ctatgggctg    6240
atgtctcata tgggactttt ctactagaga gcctacgtta ctttaccatt atattgtatt    6300
ctttgagaca ttattattat ttttttacct tttgaggaca ctctttttt gtatttgaag     6360 gaatttattg tttattttgt ttggaatatg tttggttgga tttattcgat tcatatatat    6420
tatataaaag taattatgtt attaagaaac gtagtaagaa cttacaaata taaggatcga    6480
atcccgaact tcatgcaaat caatttacaa cccacacaag tttaacatta aattaacgtg    6540
attggttagt aaattcatgt ttctctgttt aatttgttga att                      6583
```

```
<210> SEQ ID NO 8
<211> LENGTH: 19
<212> TYPE: DNA
<213> ORGANISM: Artificial Sequence
<220> FEATURE:
<223> OTHER INFORMATION: Primer

<400> SEQUENCE: 8
tcccggacat gaagccatt                                                  19

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
tgttatcact gcggtttggc                                                 20

<210> SEQ ID NO 10
<211> LENGTH: 21
<212> TYPE: DNA
<213> ORGANISM: Artificial Sequence
<220> FEATURE:
<223> OTHER INFORMATION: Probe
```

```
<400> SEQUENCE: 10
caattgaaga gactcagggt g                                         21

<210> SEQ ID NO 11
<211> LENGTH: 25
<212> TYPE: DNA
<213> ORGANISM: Artificial Sequence
<220> FEATURE:
<223> OTHER INFORMATION: Primer

<400> SEQUENCE: 11
agactcaggg tgttgttatc actgc                                     25

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
cattgctgat ccatgtagat ttcc                                      24

<210> SEQ ID NO 13
<211> LENGTH: 20
<212> TYPE: DNA
<213> ORGANISM: Artificial Sequence
<220> FEATURE:
<223> OTHER INFORMATION: Probe

<400> SEQUENCE: 13
acatgaagcc atttacaatt                                           20

<210> SEQ ID NO 14
<211> LENGTH: 20
<212> TYPE: DNA
<213> ORGANISM: Artificial Sequence
<220> FEATURE:
<223> OTHER INFORMATION: Probe

<400> SEQUENCE: 14
atgttgagta tgtcaaatga                                           20

<210> SEQ ID NO 15
<211> LENGTH: 26
<212> TYPE: DNA
<213> ORGANISM: Artificial Sequence
<220> FEATURE:
<223> OTHER INFORMATION: Primer

<400> SEQUENCE: 15
gaaacaaagg atctcaaacc attctt                                    26

<210> SEQ ID NO 16
<211> LENGTH: 40
<212> TYPE: DNA
<213> ORGANISM: Glycine max

<400> SEQUENCE: 16
aaccattctt tatgttgagt atgtcaaatg aagagactca                     40

<210> SEQ ID NO 17
<211> LENGTH: 2370
<212> TYPE: DNA
<213> ORGANISM: Glycine max
```

```
<220> FEATURE:
<221> NAME/KEY: misc_feature
<222> LOCATION: (115)..(115)
<223> OTHER INFORMATION: n is a, c, g, or t
<220> FEATURE:
<221> NAME/KEY: misc_feature
<222> LOCATION: (155)..(155)
<223> OTHER INFORMATION: n is a, c, g, or t
<220> FEATURE:
<221> NAME/KEY: misc_feature
<222> LOCATION: (434)..(434)
<223> OTHER INFORMATION: n is a, c, g, or t

<400> SEQUENCE: 17
gggtgttgtt atcactgcgg tttggccttt gggccaaggc actgttgtcc tgaaaaaaat      60
atgagagttg taatactcgc taaggatgag tagattaatg aagacgggga gatcntagga     120
ttaaaaaatg agaatgagga agaatgtgag gaagntttgg agatggtttg ctagcggatg     180
gatttgtcag tttgttccgc aggtgggcta acccagcctc aagcatgaag cttaggtgag     240
aattataggg gcaagaggtg ataatcttga ttgacaatag ggcaagccac aactttatat     300
ccaacaaatt ggtacataaa ttgggactca gcatagatcc cacaaagccc tattatatga     360
gattggggga tagtaaccgc aaatccactc aaggatgttg taagaactta aaaaatagtt     420
gggagcttat accntggtag gatatttcta tctatttaag ttgggaggag tggacctaat     480
tattggagtt gcttagttgg aaacattggg agaaattaag gtgaattgga ggaccctaag     540
tatgtctttt gtccaccaag atcagaatat ggtgatcaag gagatcttgg tttattgaag     600
acaatgatca ttttgagaac attgcaaaaa atagttagca aggaagttga gatgatgttc     660
atgttgtggg taattgaaag caactatgtg gaacaaattg atttaacaaa gaaccaagaa     720
aattagttgt agcaagtact gatagagttt gctacagttt ttcaggacct aagggtttac     780
caccatctag agaggttgat cacaagattg caattaagtc cggggcatat ccagataatg     840
ttaggcctta tcgttacccc cacttacaga agaatgagat aaaaactcta gtggttgaga     900
tgttatgatt ggggattatt agactaagca atagctccta ttctagccca gtaattttgg     960
taaaaaggaa agatggaagt tgacgattat gtatggatta tcaggcttta agtaaggcta    1020
cagtcccaga caagttcctg attcctgtca tgaaagagtt gttggatgag ttaaatggac    1080
ccatccactt ctctaaaata gatctaaagg caaggtatca ccaaatcaga atgcacaaac    1140
ctaccttcag aactcaccaa ggacattatg aatctccagt gatgccattt ggattaacaa    1200
acaccccgac cacgttccaa tgagctatga atgccacact gaaaccgttc cttcgtaggt    1260
atgtggtagt gttctttgat gacatttttgg tctatagtaa gtcttgggaa gcccatttgg    1320
atcatttgag ttaggtgttg gccaggttat tagaacatta tttcttcaca aatgttttta    1380
aaaaaaaatg tagttttggt caaattaagg cgggttgctt agggcacgtt atctctaaag    1440
aaggagtttt gatgaggcca ttttgtagtg gccaatgcct aaaactccta agtctttgag    1500 agggttttg gaacttacag gttattataa aaggtccatt tgcaattatg ggaagatagc    1560
tcgcccattg attgatctat taaagtaagg aaattttaag tggaatgagg atagtattaa    1620
ggcttccata caattacaac aagctattac cacaatacca acactatcca tgcttgattt    1680
ttcaaaacaa ttctccatag aatgtgatgc ctcggggaag ggaattggag ttgttctaac    1740
acaagataga aagcaaattg cttatttcaa caaggcatta aaagatttga ctctttctaa    1800
atctatgtat gaaaaggaat caatggctct tgtcttagcc atacaacatt ggaggcctta    1860
tcttccggat tagaaattta ctatatacat tgaccaaaaa agtttgagat atctactaga    1920
```

```
tcagcgaatt acaactcaac caacaatatt gggtagccaa gttgctgggg tatgagtttg   1980
acattgtgta taaggtgggg gcttcaaaca aggttgttga tgctctatct agaagagatg   2040
aagacaaaga attgcagggc atttctagac ctttctggaa agacataaca aaaattaatg   2100
aagaagttca gaaggatccc gcgttggcta aaatccgaga agaattgaag gataatctag   2160
attcacaccc tcagtacacc ctggagtgtg acatattata cttcagaggg aggttggtcc   2220
tattagcttc ttcattgtgg attccaaagt tactacaaga attccagact tctcttatgg   2280
gagggcactc gggtatttac ataacttata gaagaatcac tcaatcgctt tattggatac   2340
caataaaggg agaaatcact aagtttgtgg                                    2370

<210> SEQ ID NO 18
<211> LENGTH: 106
<212> TYPE: DNA
<213> ORGANISM: Artificial Sequence
<220> FEATURE:
<223> OTHER INFORMATION: RB/RB junction

<400> SEQUENCE: 18
cagaactttt atcaaccagt cctgcaggtt taaactatca gtgtttgaaa atggcttcat     60
gtccgggaaa tctacatgga tcagcaaagg tagatcatca tcatgc                  106

<210> SEQ ID NO 19
<211> LENGTH: 27
<212> TYPE: DNA
<213> ORGANISM: Artificial Sequence
<220> FEATURE:
<223> OTHER INFORMATION: Primer

<400> SEQUENCE: 19
ctgaccttgt tgaggctttg gactgag                                        27

<210> SEQ ID NO 20
<211> LENGTH: 30
<212> TYPE: DNA
<213> ORGANISM: Artificial Sequence
<220> FEATURE:
<223> OTHER INFORMATION: Primer

<400> SEQUENCE: 20
ggaacagtag tttactttga ttgaagattc                                     30
```